US010583228B2

(12) United States Patent
Shuler et al.

(10) Patent No.: US 10,583,228 B2
(45) Date of Patent: Mar. 10, 2020

(54) SUB-ATMOSPHERIC WOUND THERAPY SYSTEMS AND METHODS

(71) Applicant: J&M Shuler Medical, Inc., Athens, GA (US)

(72) Inventors: Michael Simms Shuler, Athens, GA (US); Lars Runquist, Inver Grove Heights, MN (US); Alan Carlson, St. Paul, MN (US); Evan Leingang, Plymouth, MN (US)

(73) Assignee: J&M Shuler Medical, Inc., Athens, GA (US)

( * ) Notice: Subject to any disclaimer, the term of this patent is extended or adjusted under 35 U.S.C. 154(b) by 600 days.

(21) Appl. No.: 14/811,104

(22) Filed: Jul. 28, 2015

(65) Prior Publication Data

US 2017/0028113 A1 Feb. 2, 2017

(51) Int. Cl.
*A61M 1/00* (2006.01)
*A61F 13/02* (2006.01)
*A61F 13/00* (2006.01)

(52) U.S. Cl.
CPC ..... *A61M 1/0058* (2013.01); *A61F 13/00068* (2013.01); *A61F 13/0216* (2013.01); *A61M 1/0088* (2013.01)

(58) Field of Classification Search
CPC .............. A61M 1/0058; A61M 1/0088; A61M 1/0084; A61M 1/005; A61M 27/00; A61F 13/00068; A61F 13/0216; A61F 13/023; A61F 2013/00536; A61F 2013/00174
See application file for complete search history.

(56) References Cited

U.S. PATENT DOCUMENTS

| | | | |
|---|---|---|---|
| 1,000,001 | A | 8/1911 | Holz |
| 1,355,846 | A | 10/1920 | Rannells |
| 1,385,346 | A | 7/1921 | Taylor |
| 1,596,754 | A | 8/1926 | Moschelle |
| 1,936,129 | A | 11/1933 | Fisk |
| 2,195,771 | A | 4/1940 | Estler |
| 2,221,758 | A | 11/1940 | Elmquist |
| 2,338,339 | A | 1/1944 | LaMere et al. |
| 2,443,481 | A | 6/1948 | Sene |
| 2,573,791 | A | 11/1951 | Howells |
| 2,577,945 | A | 12/1951 | Atherton |
| 2,632,443 | A | 3/1953 | Lesher |
| 2,682,873 | A | 7/1954 | Evans et al. |
| 3,026,874 | A | 3/1962 | Stevens |

(Continued)

FOREIGN PATENT DOCUMENTS

| | | |
|---|---|---|
| CN | 103623496 | 3/2014 |
| EP | 1304966 | 5/2003 |

(Continued)

OTHER PUBLICATIONS

U.S. Appl. No. 60/853,000, filed Oct. 20, 2006, Freedman.

(Continued)

*Primary Examiner* — Kevin C Sirmons
*Assistant Examiner* — Alexandra Lalonde
(74) *Attorney, Agent, or Firm* — Fish & Richardson P.C.

(57) ABSTRACT

Some embodiments of a multi-layered dressing system for sealed wound treatment include various components used for sealing, dressing, suctioning and irrigating that are coupled together as a single, composite unit.

25 Claims, 14 Drawing Sheets

(56) References Cited

U.S. PATENT DOCUMENTS

| | | |
|---|---|---|
| 3,315,665 A | 4/1967 | MacLeod |
| 3,367,332 A | 2/1968 | Groves |
| 3,382,867 A | 5/1968 | Reaves |
| 3,520,300 A | 7/1970 | Flower, Jr. |
| 3,528,416 A | 9/1970 | Chamberlain |
| 3,568,675 A | 3/1971 | Harvey |
| 3,599,830 A | 8/1971 | Gilchrist et al. |
| 3,610,238 A | 10/1971 | Rich |
| 3,648,692 A | 3/1972 | Wheeler |
| 3,782,377 A | 1/1974 | Rychlik |
| 3,812,972 A | 5/1974 | Rosenblum |
| 3,814,095 A | 6/1974 | Lubens |
| 3,831,588 A | 8/1974 | Rindner |
| 3,874,387 A | 4/1975 | Barbieri |
| 3,903,882 A | 9/1975 | Augurt |
| 3,935,863 A | 2/1976 | Kliger |
| 3,954,105 A | 5/1976 | Nordby et al. |
| 4,080,970 A | 3/1978 | Miller |
| 4,112,947 A | 9/1978 | Nehring |
| 4,139,004 A | 2/1979 | Gonzalez, Jr. |
| 4,149,541 A | 4/1979 | Gammons et al. |
| 4,178,974 A | 12/1979 | Levin |
| 4,191,204 A | 3/1980 | Nehring |
| 4,224,941 A | 9/1980 | Stivala |
| 4,250,882 A | 2/1981 | Adair |
| 4,275,721 A | 6/1981 | Olson |
| 4,297,995 A | 11/1981 | Golub |
| 4,341,209 A | 7/1982 | Schaar |
| 4,373,519 A | 2/1983 | Errede et al. |
| 4,382,441 A | 5/1983 | Svedman |
| 4,399,816 A | 8/1983 | Spangler |
| 4,457,755 A | 7/1984 | Wilson |
| 4,460,354 A | 7/1984 | Weilbacher et al. |
| 4,460,370 A | 7/1984 | Allison et al. |
| 4,465,062 A | 8/1984 | Versaggi et al. |
| 4,469,092 A | 9/1984 | Marshall et al. |
| 4,559,035 A | 12/1985 | Benjamin et al. |
| 4,608,041 A | 8/1986 | Nielsen |
| 4,624,656 A | 11/1986 | Clark et al. |
| 4,633,863 A | 1/1987 | Filips et al. |
| 4,637,819 A | 1/1987 | Ouellette et al. |
| 4,641,643 A | 2/1987 | Greer |
| 4,655,754 A | 4/1987 | Richmond et al. |
| 4,661,093 A | 4/1987 | Beck et al. |
| 4,664,652 A | 5/1987 | Weilbacher |
| 4,664,662 A | 5/1987 | Webster |
| 4,667,666 A | 5/1987 | Fryslie |
| 4,679,590 A | 7/1987 | Hergenroeder |
| 4,717,382 A | 1/1988 | Clemens et al. |
| 4,733,659 A | 3/1988 | Edenbaum et al. |
| 4,740,202 A | 4/1988 | Stacey et al. |
| 4,743,232 A | 5/1988 | Kruger |
| 4,747,166 A | 5/1988 | Kuntz |
| 4,759,354 A | 7/1988 | Quarfoot |
| 4,765,316 A | 8/1988 | Marshall |
| 4,778,446 A | 10/1988 | Jensen |
| 4,778,456 A | 10/1988 | Lokken |
| 4,820,265 A | 4/1989 | DeSatnick et al. |
| 4,820,284 A | 4/1989 | Hauri |
| 4,834,110 A | 5/1989 | Richard |
| 4,872,450 A | 10/1989 | Austad |
| 4,886,502 A | 12/1989 | Poirier et al. |
| 4,897,081 A | 1/1990 | Poirier et al. |
| 4,906,240 A | 3/1990 | Reed et al. |
| 4,915,694 A | 4/1990 | Yamamoto et al. |
| 4,917,112 A | 4/1990 | Kalt |
| 4,921,492 A | 5/1990 | Schultz et al. |
| 4,930,997 A | 6/1990 | Bennett |
| 4,941,882 A | 7/1990 | Ward et al. |
| 4,953,565 A | 9/1990 | Tachibana et al. |
| 4,890,608 A | 10/1990 | Steer |
| 4,962,761 A | 10/1990 | Golden |
| 4,969,880 A | 11/1990 | Zamierowski |
| 4,969,881 A | 11/1990 | Viesturs |
| 4,988,336 A | 1/1991 | Kohn |
| 4,990,144 A | 2/1991 | Blott |
| 4,991,574 A | 2/1991 | Pocknell |
| 4,997,425 A | 3/1991 | Shioya et al. |
| 5,002,528 A | 3/1991 | Palestrant |
| 5,002,529 A | 3/1991 | Cunningham |
| 5,003,971 A | 4/1991 | Buckley |
| 5,014,389 A | 5/1991 | Ogilvie et al. |
| 5,034,003 A | 7/1991 | Denance |
| 5,034,006 A | 7/1991 | Hosoda et al. |
| 5,042,978 A | 8/1991 | Quenin et al. |
| 5,045,777 A | 9/1991 | Itagaki |
| 5,060,662 A | 10/1991 | Farnsworth, III |
| 5,071,409 A | 12/1991 | Rosenberg |
| 5,073,172 A | 12/1991 | Fell |
| 5,086,763 A | 2/1992 | Hathman |
| 5,086,764 A | 2/1992 | Gillman |
| 5,100,396 A | 3/1992 | Zamierowski |
| 5,101,808 A | 4/1992 | Kobayashi et al. |
| 5,106,362 A | 4/1992 | Gilman |
| 5,106,629 A | 4/1992 | Cartmell et al. |
| 5,135,518 A | 4/1992 | Vera |
| 5,147,338 A | 9/1992 | Lang et al. |
| 5,149,331 A | 9/1992 | Ferdman et al. |
| 5,152,757 A | 10/1992 | Eriksson |
| 5,160,322 A | 11/1992 | Scheremet et al. |
| 5,167,613 A | 12/1992 | Karami et al. |
| 5,170,781 A | 12/1992 | Loomis |
| 5,176,502 A | 1/1993 | Sanderson et al. |
| 5,176,663 A | 1/1993 | Svedman et al. |
| 5,176,667 A | 1/1993 | DeBring |
| 5,215,539 A | 6/1993 | Schoolman |
| 5,228,431 A | 7/1993 | Giarretto |
| 5,230,350 A | 7/1993 | Fentress |
| 5,238,654 A | 8/1993 | Nohl et al. |
| 5,261,893 A | 11/1993 | Zamierowski |
| 5,263,922 A | 11/1993 | Soya et al. |
| 5,291,887 A | 3/1994 | Stanley et al. |
| 5,298,015 A | 3/1994 | Komatsuzaki et al. |
| 5,330,452 A | 7/1994 | Zook |
| 5,344,415 A | 9/1994 | DeBusk et al. |
| 5,349,965 A | 9/1994 | McCarver |
| 5,358,494 A | 10/1994 | Svedman |
| 5,374,254 A | 12/1994 | Buma |
| 5,376,252 A | 12/1994 | Ekstrom et al. |
| 5,395,315 A | 3/1995 | Griep |
| 5,419,768 A | 5/1995 | Kayser |
| 5,431,622 A | 7/1995 | Pyrozyk et al. |
| 5,437,651 A | 8/1995 | Todd et al. |
| 5,445,604 A | 8/1995 | Lang |
| 5,451,215 A | 9/1995 | Wolter |
| 5,478,333 A | 12/1995 | Asherman, Jr. |
| 5,484,420 A | 1/1996 | Russo |
| 5,484,427 A | 1/1996 | Gibbons |
| 5,484,428 A | 1/1996 | Drainville et al. |
| 5,487,889 A | 1/1996 | Eckert et al. |
| 5,520,652 A | 5/1996 | Peterson |
| 5,527,293 A | 6/1996 | Zamierowski |
| 5,531,670 A | 7/1996 | Westby et al. |
| 5,533,981 A | 7/1996 | Mandro et al. |
| 5,542,918 A | 8/1996 | Atkinson |
| 5,549,584 A | 8/1996 | Gross |
| 5,556,375 A | 9/1996 | Ewall |
| 5,578,022 A | 11/1996 | Scherson et al. |
| 5,607,388 A | 3/1997 | Ewall |
| 5,624,418 A | 4/1997 | Shepard |
| 5,628,735 A | 5/1997 | Skow |
| 5,636,643 A | 6/1997 | Argenta et al. |
| 5,645,081 A | 7/1997 | Argenta et al. |
| 5,655,258 A | 8/1997 | Heintz |
| 5,656,027 A | 8/1997 | Ellingboe |
| 5,660,350 A | 8/1997 | Byrne et al. |
| 5,662,598 A | 9/1997 | Tobin |
| 5,662,624 A | 9/1997 | Sundstrom et al. |
| 5,662,625 A | 9/1997 | Westwood |
| 5,669,892 A | 9/1997 | Keogh et al. |
| 5,672,152 A | 9/1997 | Mason et al. |
| 5,678,564 A | 10/1997 | Lawrence et al. |
| 5,690,815 A | 11/1997 | Krasnoff et al. |
| 5,697,920 A | 12/1997 | Gibbons |

(56) References Cited

U.S. PATENT DOCUMENTS

| | | |
|---|---|---|
| 5,735,833 A | 4/1998 | Olson |
| 5,741,237 A | 4/1998 | Walker |
| 5,755,706 A | 5/1998 | Kronenthal et al. |
| 5,759,570 A | 6/1998 | Arnold |
| 5,762,640 A | 6/1998 | Kajiwara et al. |
| 5,782,871 A | 7/1998 | Fujiwara et al. |
| 5,817,145 A | 10/1998 | Augustine et al. |
| 5,827,246 A | 10/1998 | Bowen |
| 5,911,222 A | 6/1999 | Lawrence et al. |
| 5,919,476 A | 7/1999 | Fischer et al. |
| 5,921,972 A | 7/1999 | Skow |
| 5,928,174 A | 7/1999 | Gibbins |
| 5,941,859 A | 8/1999 | Lerman |
| 5,947,914 A | 9/1999 | Augustine |
| 5,954,680 A | 9/1999 | Augustine |
| 5,961,480 A | 10/1999 | Augustine |
| 5,964,721 A | 10/1999 | Augustine |
| 5,964,723 A | 10/1999 | Augustine |
| 5,986,163 A | 11/1999 | Augustine |
| 6,010,527 A | 1/2000 | Augustine et al. |
| 6,017,493 A | 1/2000 | Cambron et al. |
| 6,039,724 A | 3/2000 | Seifert et al. |
| 6,045,518 A | 4/2000 | Augustine |
| 6,045,541 A | 4/2000 | Matsumoto et al. |
| 6,048,337 A | 4/2000 | Svedman |
| 6,056,730 A | 5/2000 | Greter |
| 6,071,254 A | 6/2000 | Augustine |
| 6,071,267 A | 6/2000 | Zamierowski |
| 6,071,304 A | 6/2000 | Augustine et al. |
| 6,080,189 A | 6/2000 | Augustine et al. |
| 6,080,243 A | 6/2000 | Insley et al. |
| 6,093,160 A | 7/2000 | Augustine et al. |
| 6,093,230 A | 7/2000 | Johnson, III et al. |
| 6,095,992 A | 8/2000 | Augustine |
| 6,110,197 A | 8/2000 | Augustine et al. |
| 6,113,561 A | 9/2000 | Augustine |
| 6,117,111 A | 9/2000 | Fleischmann |
| 6,135,116 A | 10/2000 | Vogel et al. |
| 6,142,982 A | 11/2000 | Hunt et al. |
| 6,143,945 A | 11/2000 | Augustine et al. |
| 6,165,994 A | 12/2000 | Henley |
| 6,174,306 B1 | 1/2001 | Fleischmann |
| 6,176,868 B1 | 1/2001 | Detour |
| 6,179,804 B1 | 1/2001 | Satterfield |
| 6,203,563 B1 | 3/2001 | Fernandez |
| 6,207,875 B1 | 3/2001 | Lindqvist et al. |
| 6,213,965 B1 | 4/2001 | Augustine et al. |
| 6,213,966 B1 | 4/2001 | Augustine |
| 6,217,535 B1 | 4/2001 | Augustine |
| 6,235,009 B1 | 5/2001 | Skow |
| 6,235,047 B1 | 5/2001 | Augustine et al. |
| 6,241,697 B1 | 6/2001 | Augustine |
| 6,241,698 B1 | 6/2001 | Augustine |
| 6,244,311 B1 | 6/2001 | Hand et al. |
| 6,244,698 B1 | 6/2001 | Hand et al. |
| 6,248,084 B1 | 6/2001 | Augustine et al. |
| 6,254,557 B1 | 7/2001 | Augustine et al. |
| 6,254,580 B1 | 7/2001 | Svedman |
| 6,264,622 B1 | 7/2001 | Augustine |
| 6,264,979 B1 | 7/2001 | Svedman |
| 6,267,740 B1 | 7/2001 | Augustine et al. |
| 6,283,931 B1 | 9/2001 | Augustine |
| 6,284,941 B1 | 9/2001 | Cox et al. |
| 6,290,685 B1 | 9/2001 | Insley et al. |
| 6,293,917 B1 | 9/2001 | Augustine et al. |
| 6,345,623 B1 | 2/2002 | Heaton et al. |
| 6,398,767 B1 | 6/2002 | Fleischmann |
| 6,458,109 B1 | 10/2002 | Henley et al. |
| 6,468,237 B1 | 10/2002 | Lina |
| 6,491,682 B2 | 12/2002 | Paderni |
| 6,645,226 B1 | 11/2003 | Jacobs et al. |
| 6,648,862 B2 | 11/2003 | Watson |
| 6,663,349 B1 | 12/2003 | Discenzo et al. |
| 6,685,681 B2 | 2/2004 | Anker et al. |
| 6,691,047 B1 | 2/2004 | Fredericks |
| 6,695,823 B1 | 2/2004 | Lina et al. |
| 6,749,592 B2 | 6/2004 | Lord |
| 6,752,794 B2 | 6/2004 | Lockwood et al. |
| 6,755,807 B2 | 6/2004 | Risk, Jr. et al. |
| 6,764,462 B2 | 7/2004 | Risk, Jr. et al. |
| 6,767,334 B1 | 7/2004 | Randolph |
| 6,800,074 B2 | 10/2004 | Henley et al. |
| 6,824,533 B2 | 11/2004 | Risk, Jr. et al. |
| 6,855,135 B2 | 2/2005 | Lockwood et al. |
| 6,893,452 B2 | 5/2005 | Jacobs |
| 6,978,816 B1 | 12/2005 | Byrne et al. |
| 6,978,884 B2 | 12/2005 | Lockwood |
| 7,004,915 B2 | 2/2006 | Boynton et al. |
| 7,022,113 B2 | 4/2006 | Lockwood et al. |
| 7,108,683 B2 | 9/2006 | Zamierowski |
| 7,117,869 B2 | 10/2006 | Heaton et al. |
| 7,128,795 B2 | 10/2006 | Byrne et al. |
| 7,156,862 B2 | 1/2007 | Jacobs et al. |
| 7,195,624 B2 | 3/2007 | Lockwood et al. |
| 7,198,046 B1 | 4/2007 | Argenta et al. |
| 7,216,651 B2 | 5/2007 | Argenta et al. |
| 7,276,051 B1 | 10/2007 | Henley et al. |
| 7,338,482 B2 | 3/2008 | Lockwood et al. |
| 7,361,184 B2 | 4/2008 | Joshi |
| 7,381,211 B2 | 6/2008 | Zamierowski |
| 7,413,571 B2 | 8/2008 | Zamierowski |
| 7,422,576 B2 | 9/2008 | Boynton et al. |
| 7,438,705 B2 | 10/2008 | Karpowicz et al. |
| 7,520,872 B2 | 4/2009 | Biggie et al. |
| 7,524,286 B2 | 4/2009 | Johnson |
| 7,524,315 B2 | 4/2009 | Blott et al. |
| 7,532,953 B2 | 5/2009 | Vogel |
| 7,534,927 B2 | 5/2009 | Lockwood et al. |
| 7,608,066 B2 | 10/2009 | Vogel |
| 7,645,269 B2 | 1/2010 | Zamierowski |
| 7,651,484 B2 | 1/2010 | Heaton et al. |
| 7,678,090 B2 | 3/2010 | Risk, Jr. et al. |
| 7,723,560 B2 | 5/2010 | Lockwood et al. |
| 7,763,000 B2 | 7/2010 | Risk, Jr. et al. |
| 7,794,438 B2 | 9/2010 | Henley et al. |
| 7,837,673 B2 | 11/2010 | Vogel |
| 7,867,206 B2 | 1/2011 | Lockwood et al. |
| 7,883,494 B2 | 2/2011 | Martin |
| 7,896,864 B2 | 3/2011 | Lockwood et al. |
| 7,922,703 B2 | 4/2011 | Riesinger |
| 7,927,318 B2 | 4/2011 | Risk, Jr. et al. |
| 7,927,352 B2 | 4/2011 | Wilke et al. |
| 7,951,100 B2 | 5/2011 | Hunt et al. |
| 7,967,810 B2 | 6/2011 | Freedman |
| 7,927,362 B2 | 7/2011 | Wilke et al. |
| 7,988,680 B2 | 8/2011 | Lockwood et al. |
| 8,057,446 B2 | 11/2011 | Kane et al. |
| 8,066,243 B2 | 11/2011 | Svedman et al. |
| 8,084,664 B2 | 12/2011 | Johnson et al. |
| 8,142,405 B2 | 3/2012 | Vogel |
| 8,162,909 B2 | 4/2012 | Blott et al. |
| 8,168,848 B2 | 5/2012 | Lockwood et al. |
| 8,187,210 B2 | 5/2012 | Hunt et al. |
| 8,350,116 B2 | 1/2013 | Lockwood et al. |
| 8,372,049 B2 | 2/2013 | Jaeb et al. |
| 8,376,972 B2 | 2/2013 | Fleischmann |
| 8,425,478 B2 | 4/2013 | Olson |
| 8,444,613 B2 | 5/2013 | Svedman et al. |
| 8,447,375 B2 | 5/2013 | Freedman et al. |
| 8,460,258 B2 | 6/2013 | Jones et al. |
| 8,460,273 B2 | 6/2013 | Freedman et al. |
| 8,974,428 B2 | 3/2015 | Freedman et al. |
| 2001/0031943 A1 | 10/2001 | Urie |
| 2002/115967 A1 | 8/2002 | Svedman |
| 2002/0143286 A1 | 10/2002 | Tumey |
| 2002/0150720 A1* | 10/2002 | Howard ............ A61M 1/0058 428/131 |
| 2002/0161346 A1* | 10/2002 | Lockwood .......... A61M 1/0058 604/315 |
| 2002/0183702 A1 | 12/2002 | Henley |
| 2003/0139255 A1 | 7/2003 | Lina |
| 2003/0163160 A1 | 8/2003 | O'Malley et al. |
| 2003/0208149 A1 | 11/2003 | Coffey |
| 2004/0006319 A1 | 1/2004 | Lina et al. |

(56) References Cited

U.S. PATENT DOCUMENTS

| | | |
|---|---|---|
| 2004/0054338 A1 | 3/2004 | Bybordi et al. |
| 2004/0064111 A1 | 4/2004 | Lockwood et al. |
| 2004/0064132 A1 | 4/2004 | Boehringer et al. |
| 2004/0243073 A1 | 12/2004 | Lockwood et al. |
| 2004/0265040 A1 | 12/2004 | Rosenberg |
| 2005/0070858 A1 | 3/2005 | Lockwood et al. |
| 2005/0085795 A1* | 4/2005 | Lockwood ......... A61M 1/0084 604/543 |
| 2006/0041238 A1 | 2/2006 | Bowen |
| 2006/0129137 A1 | 6/2006 | Lockwood et al. |
| 2006/0282028 A1 | 12/2006 | Howard et al. |
| 2007/0038247 A1 | 2/2007 | Lebner et al. |
| 2007/0167926 A1 | 7/2007 | Blott et al. |
| 2007/0225634 A1 | 9/2007 | Ferren et al. |
| 2007/0225663 A1 | 9/2007 | Watt et al. |
| 2007/0233022 A1 | 10/2007 | Henley et al. |
| 2008/0041401 A1 | 2/2008 | Casola et al. |
| 2008/0167593 A1 | 7/2008 | Fleischmann |
| 2008/0208011 A1 | 8/2008 | Shuler |
| 2009/0082740 A1 | 3/2009 | Lockwood et al. |
| 2009/0177051 A1 | 7/2009 | Arons et al. |
| 2009/0221977 A1 | 9/2009 | Blott et al. |
| 2010/0057022 A1 | 3/2010 | Horrigan |
| 2010/0063483 A1 | 3/2010 | Adahan |
| 2010/0174250 A1* | 7/2010 | Hu ....................... A61F 5/4401 604/319 |
| 2010/0185236 A1 | 7/2010 | Elliott et al. |
| 2010/0191196 A1 | 7/2010 | Heagle |
| 2010/0191198 A1 | 7/2010 | Heagle |
| 2010/0262091 A1 | 10/2010 | Larsson |
| 2010/0280428 A1 | 11/2010 | Widgerow et al. |
| 2010/0292549 A1 | 11/2010 | Shuler |
| 2011/0034888 A1 | 2/2011 | Aali |
| 2011/0054283 A1 | 3/2011 | Shuler |
| 2011/0106026 A1 | 5/2011 | Wu et al. |
| 2011/0125110 A1 | 5/2011 | Cotton |
| 2011/0172617 A1 | 7/2011 | Riesinger |
| 2011/0213319 A1 | 9/2011 | Blott et al. |
| 2012/0041403 A1 | 2/2012 | Bennett et al. |
| 2012/0316518 A1 | 12/2012 | Croizt et al. |
| 2013/0096520 A1 | 4/2013 | Lockwood et al. |
| 2013/0138060 A1 | 5/2013 | Haggstrom et al. |
| 2013/0144230 A1 | 6/2013 | Wu et al. |
| 2013/0165821 A1 | 6/2013 | Freedman et al. |
| 2013/0165878 A1 | 6/2013 | Heagle |
| 2013/0172834 A1 | 7/2013 | Heagle |
| 2013/0274695 A1 | 10/2013 | Freedman et al. |
| 2014/0018752 A1 | 1/2014 | Shuler et al. |
| 2014/0052083 A1 | 2/2014 | Freedman |
| 2014/0066868 A1* | 3/2014 | Freedman ......... A61F 13/00063 604/319 |
| 2014/0221907 A1* | 8/2014 | Scholz .............. A61F 13/00063 604/25 |

FOREIGN PATENT DOCUMENTS

| | | |
|---|---|---|
| WO | WO 1997/005838 | 2/1997 |
| WO | WO 2003/057070 | 7/2003 |
| WO | WO 2006/114648 | 11/2006 |
| WO | WO 2007/041642 | 4/2007 |
| WO | WO 2008/106396 | 4/2008 |
| WO | WO 2008/100440 | 8/2008 |
| WO | WO 2009/062327 | 5/2009 |
| WO | WO 2009/093116 | 7/2009 |
| WO | WO 2009/141820 | 11/2009 |
| WO | WO 2010/129528 | 11/2010 |
| WO | WO 2011/091045 | 7/2011 |
| WO | WO 2013/066694 | 5/2013 |

OTHER PUBLICATIONS

U.S. Appl. No. 61/643,840, filed May 7, 2012, Freedman.
U.S. Appl. No. 61/554,080, filed Nov. 1, 2011, Freedman.
U.S. Appl. No. 61/245,789, filed Sep. 25, 2009, Shuler.
U.S. Appl. No. 61/234,857, filed Aug. 18, 2009, Shuler.
U.S. Appl. No. 61/223,797, filed Aug. 13, 2009, Shuler.
Argenta et al., "Vacuum-Assisted Closure: A New Method for Wound Control and Treatment: Clinical Experience," *Annals of Plastic Surgery*, 1997, 38(6): 563-577.
Barker et al., "Vacuum pack technique of temporary abdominal closure: a 7-year experience with 112 patients," J Trauma, Feb. 2000, 48(2): 201-6.
Barnea et al., "Our experience with Wisebands: a new skin and soft-tissue stretch device," Plast Reconstr Surg, Mar. 2004, 113(3): 862-9.
Brock et al., "Temporary Closure of Open Abdominal Wounds: The Vacuum Pack," *Am Surg.*, 1995, 61(1): 30-35.
Buckman, "Vacuum Assisted Wound Closure System," *Drexel University white paper*, Jul. 15, 2006.
Campbell, "Surgical wound case studies with the versatile 1 wound vacuum system for negative pressure wound therapy," J Wound Ostomy Continence Nurs, Mar. 2006, 33(2): 176-85.
Chariker et al., "An algorithmic approach to the use of gauze-based negative-pressure wound therapy as a bridge to closure in pediatric extremity trauma," Plast Reconstr Surg, May 2009, 123(5): 1510-20.
Chariker et al., "Effective management of incisional and cutaneous fistulae with closed suction wound drainage," Contemp Surg 1989;34:59-63.
Davydov et al., "Concepts for Clinical Biological Management of the Wound Process in the Treatment of Purulent Wounds Using Vacuum Therapy," *The Kremlin Papers; Perspectives in Wound Care from the Russian Medical Journal*, 1991, 132-135.
Davydov et al., "The Bacteriological and Cytological Assessment of Vacuum Therapy of Purulent Wounds," *The Kremlin papers, Perspectives in Wound Care from the Russian Medical Journal*, 1988, 48-52.
Davydov et al., "Vacuum Therapy in the Treatment of Purulent lactation Mastitis," *The Kremlin papers, perspectives in Wound Care from the Russian Medical Journal*, 1986, 66-70.
European Search Report for EP App. No. 10822386.8, dated Jul. 22, 2014, 7 pages.
Giovinco et al., "Wound chemotherapy by the use of negative pressure wound therapy and infusion," Eplasty, Jan. 2010, 8(10): e9.
International Preliminary Report on Patentability for PCT/US2010/045262, dated Feb. 14, 2012, 6 pages.
International Preliminary Report on Patentability in International Application No. PCT/US2012/061770, dated May 6, 2014, 12 pages.
International Search Report and Written Opinion for PCT/US2010/045262, dated Jun. 17, 2011, 7 pages.
International Search Report in International Application No. PCT/US2012/061770, dated Mar. 2, 2012, 3 pages.
Jeter, "Closed suction wound drainage system," J Wound Ostomy Continence Nurs, Mar. 2004, 31(2): 51.
Kostiuchenok et al., "The Vacuum Effect in the Surgical Treatment of Purulent Wounds," *The Kremlin Papers, Perspectives in Wound Care from the Russian Medical* Journal, 1986, 18-21.
Leininger et al., "Experience with wound VAC and delayed primary closure of contaminated soft tissue injuries in Iraq," J Trauma, Nov. 2006, 61(5): 1207-11.
'o-wm.com' [online]. "Negative pressure wound therapy: "a rose by any other name"," Mar. 2005, [retrieved on Nov. 19, 2015]. Retrieved from the Internet: URL http://www.o-wm.com/content/negative-pressure-wound-therapy-%E2%80%9Ca-rose-any-other-name%E2%80%9D, 10 pages.
Miller MS, Ortegon M, McDaniel C, Serena T. Negative pressure wound therapy: An option for hard-to-heal wounds. J Wound Care 2006;15(7): 321-324.
Morykwas et al., "Vacuum-assisted closure: state of basic research and physiologic foundation," Plast Reconstr Surg, Jun. 2006, 117(7 Suppl): 121S-126S.
Morykwas et al., "Vacuum-Assisted Closure: A New Method for Wound Control and Treatment: Basic Foundation," Annals of Plastic Surgery, 1997, 38(6): 553-562.

(56) References Cited

OTHER PUBLICATIONS

Perez et al., "Modern wound care for the poor: a randomized clinical trial comparing the vacuum system with conventional saline-soaked gauze dressings," The American Journal of Surgery, 2010, 199: 14-20.
Pliakos et al., "Vacuum-assisted closure in severe abdominal sepsis with or without retention sutured sequential fascial closure: a clinical trial," Surgery, Nov. 2010, 148(5): 947-53.
Scherer et al., "The vacuum assisted closure device: A method for securing skin grafts and improving graft survival," *Arch Surg.*, 2002, 137(8): 930-933.
Singh et al., "Dynamic Wound Closure for Decompressive Leg Fasciotomy Wounds," *Am Surg*, 2008, 74(3): 217-220.
Svedman et al., "A dressing system providing fluid supply and suction drainage used for continuous or intermittent irrigation," Ann Plast Surg, Aug. 1986, 17(2): 125-33.
Thai et al., "Ultraviolet light C in the treatment of chronic wounds with MRSA: a case study," Ostomy Wound Manage, Nov. 2002, 48(11): 52-60.
Usupov et al., "Active Wound Drainage," *The Kremlin Papers, Perspectives in Wound Care from the Russian Medical Journal*, 1987, 42-45.
Utz et al., "Metalloproteinase expression is associated with traumatic wound failure," J Surg Res, Apr. 2010, 159(2): 633-9.
Valenta, "Using the Vacuum Dressing Alternative for Difficult Wounds," *American J. of Nursing*, 1994, 44-45.
Van der Velde and Hudson, "VADER (vacuum-assisted dermal recruitment: a new method of wound closure," *Annals of Plastic Surgery*, 2005, 55(6): 660-664.
Wackenfors, et al., "Effects of vacuum-assisted closure therapy on inguinal wound edge microvascular blood flow," *Wound Repaire and Regeneration*, 2004, 12(6): 600-606.
Webb, "New Techniques in Wound Management: Vacuum-assisted Wound Closure," *J. Am Acad Orthop Surg*, 2002, 10(5): 303-311.
Wolvos, "Wound instillation—the next step in negative pressure wound therapy. Lessons learned from initial experiences.," Ostomy Wound Manage, Nov. 2004, 50(11): 56-66.
Zannis et al, "Comparison of Fasciotomy Wound Closures Using Traditional Dressing Changes and the Vacuum-assisted Closure Device," *Annals of Plastic Surgery*, 2009, 62(4): 407-409.
Zorilla, et al, "Shoelace technique for gradual closure of fasciotomy wounds," *The Journal of Trama*, 2005, 59(6): 1515-1517.
International Search Report and Written Opinion in Application No. PCT/US2016/044014, dated Oct. 18, 2016, 7 pages.
Polymer Science, Inc., "P-Derm Hydrogels," Nov. 29, 2014, Retrieved from the Internet on Dec. 29, 2016: URL: <https://web.archive.org/web/20141129100425/http://www.polymerscience.com/products/hydrogel/>, 2 pages.
Thomas, "Silicones in Medical Applications," Dow Coring Europe SA, Sep. 8, 2011, Retrieved from the Internet on Dec. 29, 2016: URL:<https://web.archive.org/web/20110908185846/http://www.dowcorning.com/content/publishedlit/Chapter17.pdf >, 9 pages.
International Preliminary Report on Patentability in International Application No. PCT/US2016/044014, dated Jan. 30, 2018, 6 pages.
European extended Search Report in European Application No. 168312288, dated Jun. 11, 2018, 8 pages.

\* cited by examiner

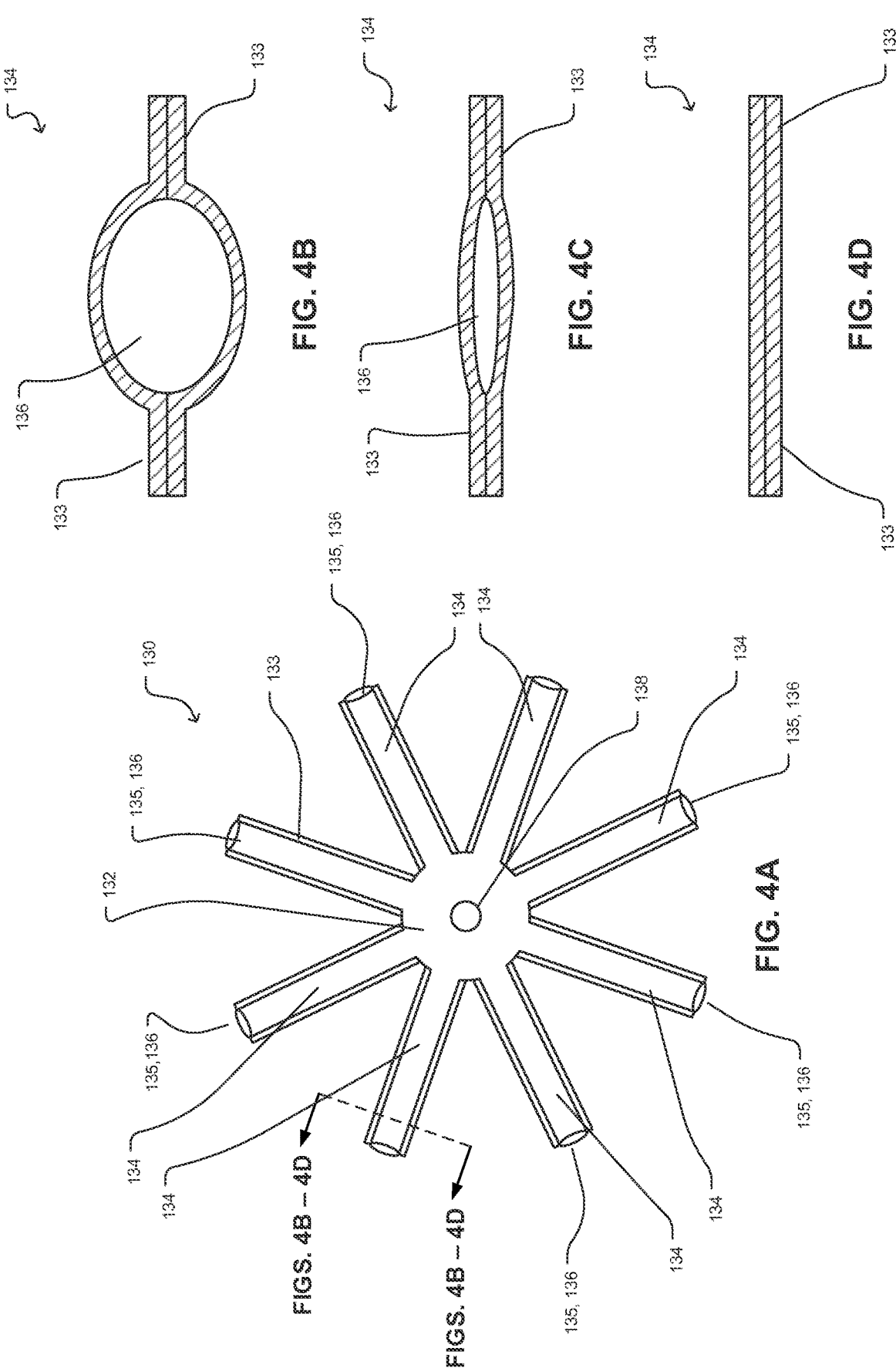

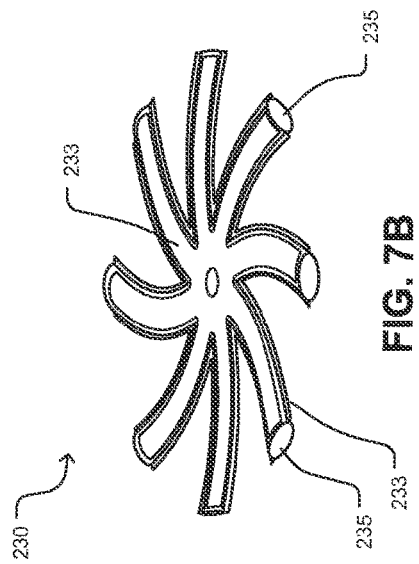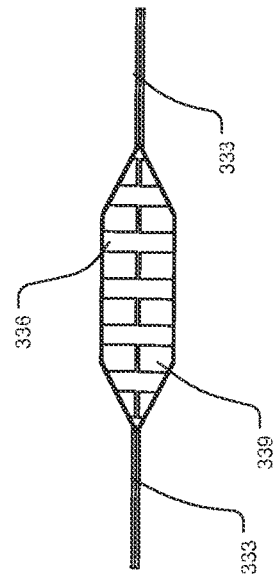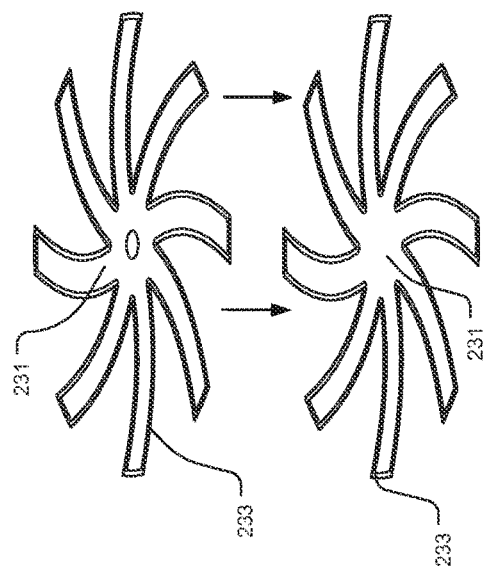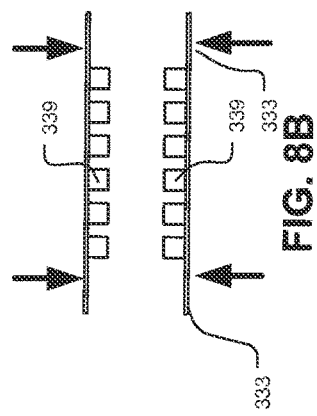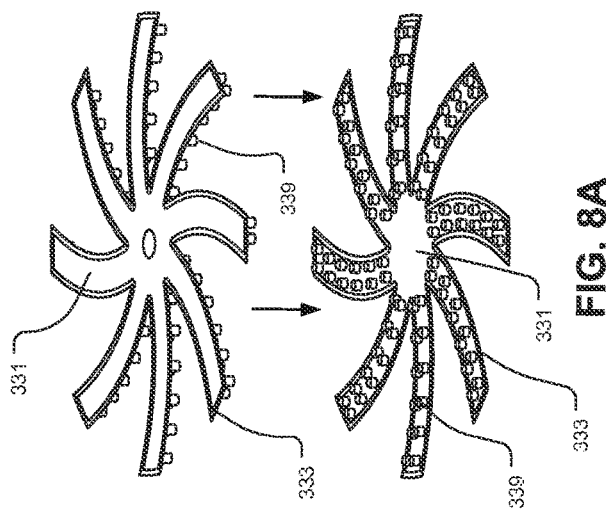

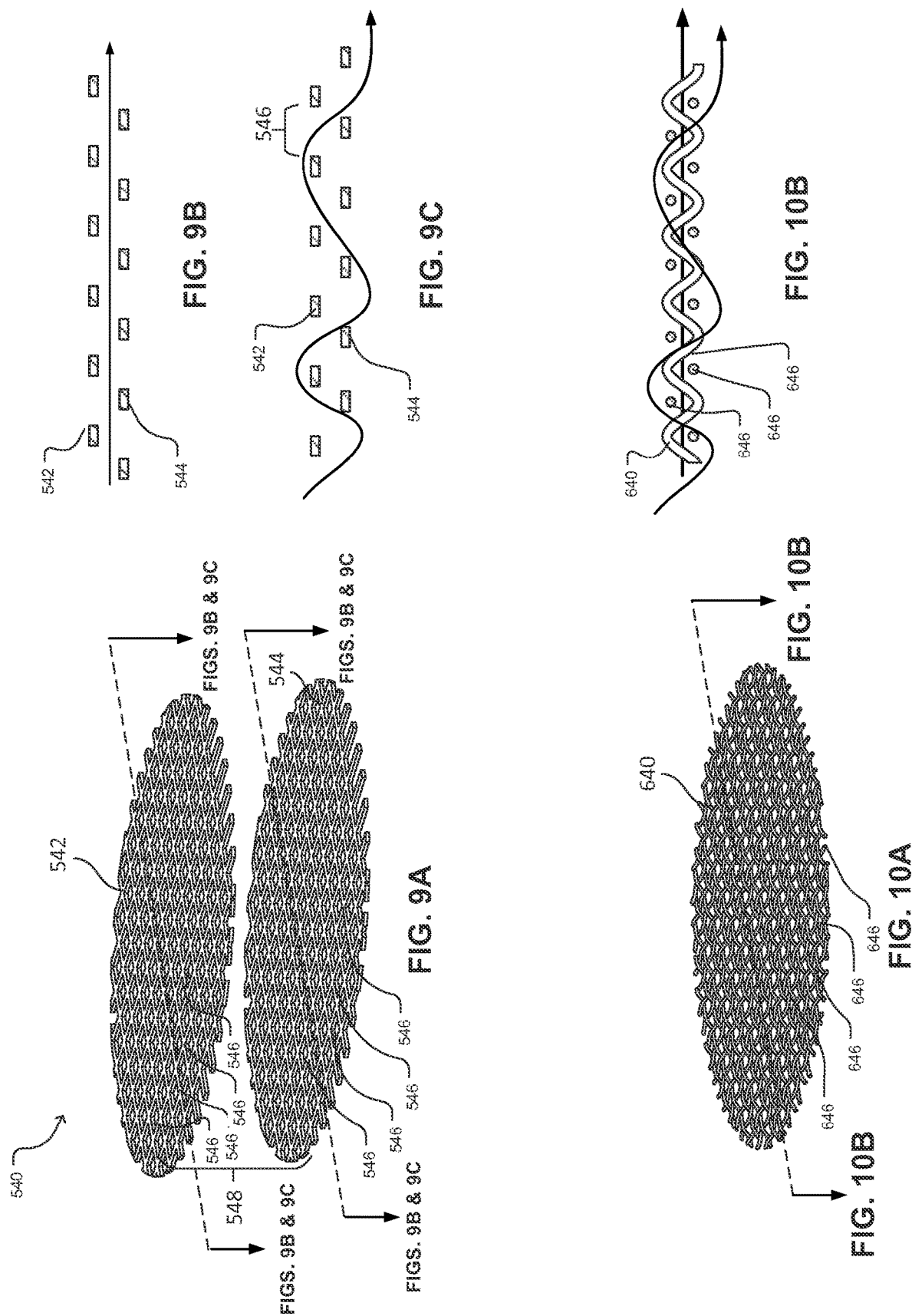

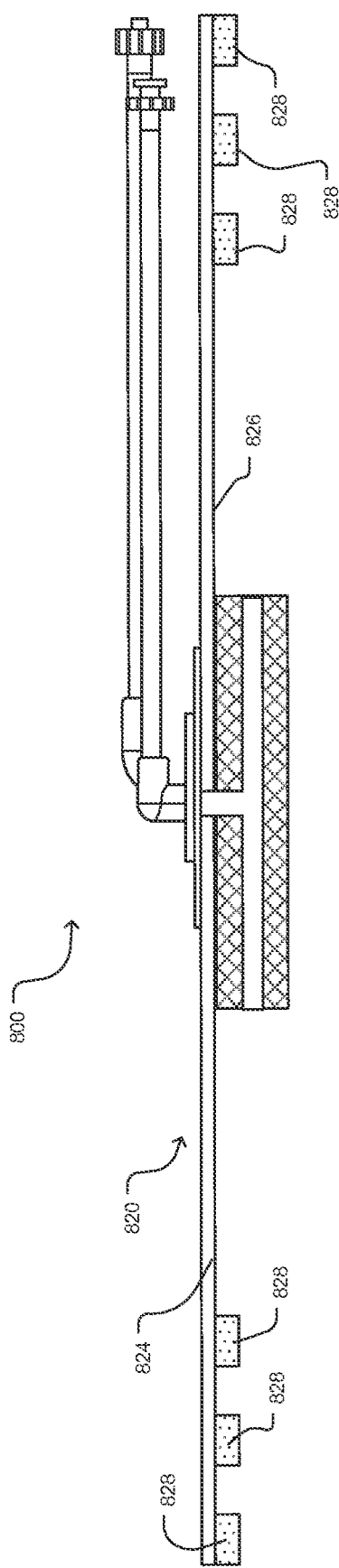
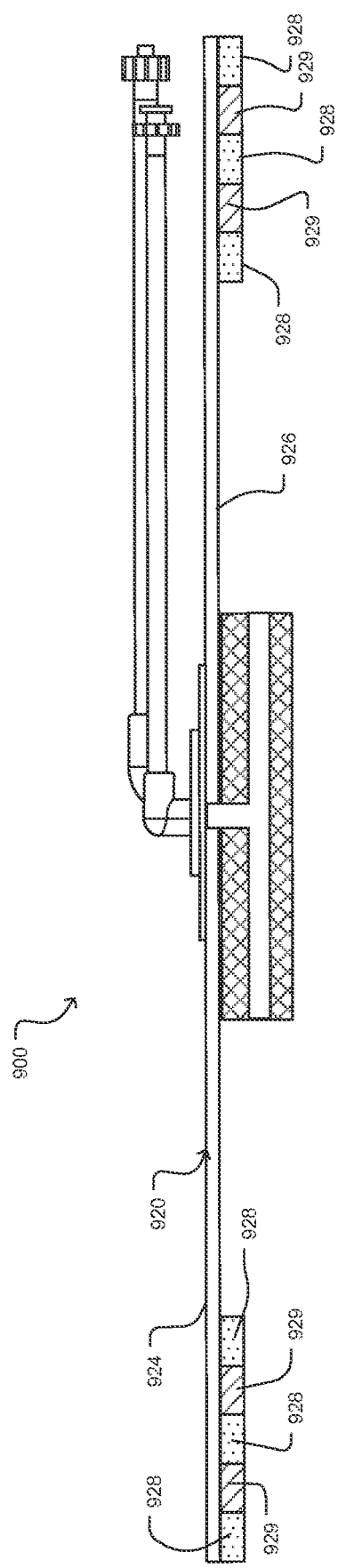

SUB-ATMOSPHERIC WOUND THERAPY SYSTEMS AND METHODS

TECHNICAL FIELD

This document relates to systems and methods for wound treatment, for example, a system or a method in which a dressing assembly is optionally applied to a wound using negative pressure therapy.

BACKGROUND

Negative-pressure wound therapy (NPWT) is a type of treatment used by physicians to promote the healing of acute or chronic wounds. For example, sealed wound dressings connected to a vacuum pump can be placed onto an open wound for applying sub-atmospheric pressure to the wound. Such types of negative-pressure applications can be used to draw out fluid from the wound and increase blood flow to a wound area. NPWT can also be used to deliver fluids, such as saline or medication, to irrigate the wound. In many instances, the sealed wound dressings include sponge or open-cell foam material that fill open cavity wounds and a film layer that covers and forms a seal over the wound. In many cases, the film layer has an opening for allowing a drainage tube residing within the wound area to be connected to a vacuum pump that, after the dressing is sealed, can be used to apply a desired pressure to the wound. In many cases, conventional therapy necessitates the assembly of the wound dressing, typically made of open-cell sponge or gauze material, at the time of application. These dressings need to be cut to size in order to fit the dressing into the contours of the wound, but often are made of materials such as polyurethane or cotton that are not easy to cut and, thus, result in multiple irregular pieces. These irregular pieces of the wound dressing may increase the chances of foreign matters being left in the wound after the dressing has been removed, and adversely affect wound healing.

SUMMARY

Some embodiments of a system described herein include providing a multi-layered dressing system for sealed wound treatment. The system described herein can be placed over a wound and create an air-tight seal with the skin located adjacent the wound. The system described herein can be configured to apply sub-atmospheric (i.e., negative pressure) suction to the wound area, and in some circumstances, to apply wound irrigation, wound debridement, or both. In one example, the system may be configured to facilitate irrigation of the surrounding tissue along the periphery of the wound by delivering saline solution or medicaments. In particular implementations, the system described herein may optionally include at least a multi-layered dressing system that integrates multiple components of the system into one system, for example, a "unified dressing assembly" (or "UDA") that integrates a port assembly, a sealing layer, and irrigation network and netting layers such that no assembly is required at application. Such implementations can be useful when treating and sealing a deep wound in a consistent and quick manner.

Various embodiments described herein may include a negative pressure wound therapy that includes a hub, a sealing layer, a perforated layer and an irrigation network. The hub can include a manifold configured for connection with an inflow line that provides a first fluid pathway to an irrigation fluid source and an outflow line that provides a second fluid pathway to a vacuum source. The sealing layer can include a film having a first surface and a second surface. In particular, in some cases, the first surface can be coupled to the hub and the second surface can include a gel adhesive disposed at one or more peripheral locations on the film. The perforated layer can be coupled to the second surface of the sealing layer and define a plurality of pores for fluid flow toward the hub. The irrigation network can be coupled to the perforated layer and include a plurality of tubes in fluid communication with the first fluid pathway. Each tube of the irrigation network can define a lumen that adjusts from a collapsed condition to an expanded condition when subjected to positive pressure.

Certain embodiments provided herein of a multilayered dressing system may include a hub, a sealing layer, a netting layer and an irrigation network. The hub can include a manifold configured for connection with an inflow line that provides a fluid pathway to an irrigation fluid source. The sealing layer can include a first surface and a second surface, the first surface being coupled to the hub. The netting layer can be coupled to the second surface of the sealing layer and define multiple openings for fluid flow toward the hub. The irrigation network can be coupled to the netting layer and include a plurality of tubes in fluid communication with the fluid pathway. Each tube of the irrigation network can define a lumen that adjusts from a collapsed condition to an expanded condition when subjected to positive pressure.

In some implementations, a multilayered dressing assembly may include a hub, a sealing layer, a netting layer, and an irrigation network. The hub can include a manifold configured for connection with an inflow line that provides a fluid pathway to an irrigation fluid source. The sealing layer can include a first surface and a second surface in which the first surface is coupled to the hub and the second surface includes a gel adhesive for adhering the assembly to skin located proximate a wound. The netting layer can be coupled to the second surface of the sealing layer. The irrigation network can be coupled to the netting layer.

Some embodiments described herein may optionally provide one or more of the following advantages. First, some of the embodiments of the systems may be configured for promoting tissue healing, monitoring, and irrigation of the wound in addition to optionally delivering therapeutic agents to the wound by providing a multi-layered UDA. Such a UDA in particular embodiments described below can reduce the likelihood or eliminate the amount of preparation time normally used for assembling together separate components of a multi-layered dressing.

Second, certain embodiments of the system described herein may provide a flexible dressing configuration that reduces the likelihood of irritation or inflammation of wound tissue during the healing. In particular, the system described herein can include an irrigation network that optionally includes flexible tubes with a collapsible lumen. As such, the tubes formed by the irrigation network can change, e.g., at least portions of the tubes of the system can flatten to partially collapse, or fully collapse into a closed state, under certain circumstances. In some implementations, the tubes can increase or decreases based on exterior forces being applied to portions of the system due to body movements by the patients, system adjustments made by a practitioner (e.g., insertion, removal or re-positioning of the system), or by changes in flowrate of the fluids being delivered therein.

Third, some embodiments of the system described herein optionally include layered portions that are readily customizable for individual patients, for example, layered portions composed of materials that can be easily cut to an appropriate size. In particular, in some examples, the portions of the system that are sealed to the wound and/or the skin can be cut to an appropriate size. In other examples, portions of the system that come into direct contact with the wound within the sealed portion of the dressing are configured for quick and easy size adjustment.

DESCRIPTION OF DRAWINGS

FIG. 4A is a top view of a first example of an irrigation network of FIG. 1. FIGS. 4B-4D are cross-sectional views of the irrigation network shown in an open state, a partially open state and a closed state, respectively.

FIGS. 7A and 7B are perspective views depicting an example process of assembling the irrigation network of FIG. 1.

FIGS. 8A-8C are perspective views depicting another example process of assembling the irrigation network of FIGS. 5A and 5B.

FIGS. 9A-9C are perspective and cross-sectional views, respectively, of perforated layers of exemplary netting layers.

FIGS. 10A and 10B are perspective and cross-sectional views, respectively, of a mesh layer of exemplary netting layers.

FIG. 13 is a cross-sectional view of a third example of a multilayered dressing system.

FIG. 14 is a cross-sectional view of a fourth example of a multilayered dressing system.

Like reference symbols in the various drawings indicate like elements.

DETAILED DESCRIPTION OF ILLUSTRATIVE EMBODIMENTS

Figure 1:
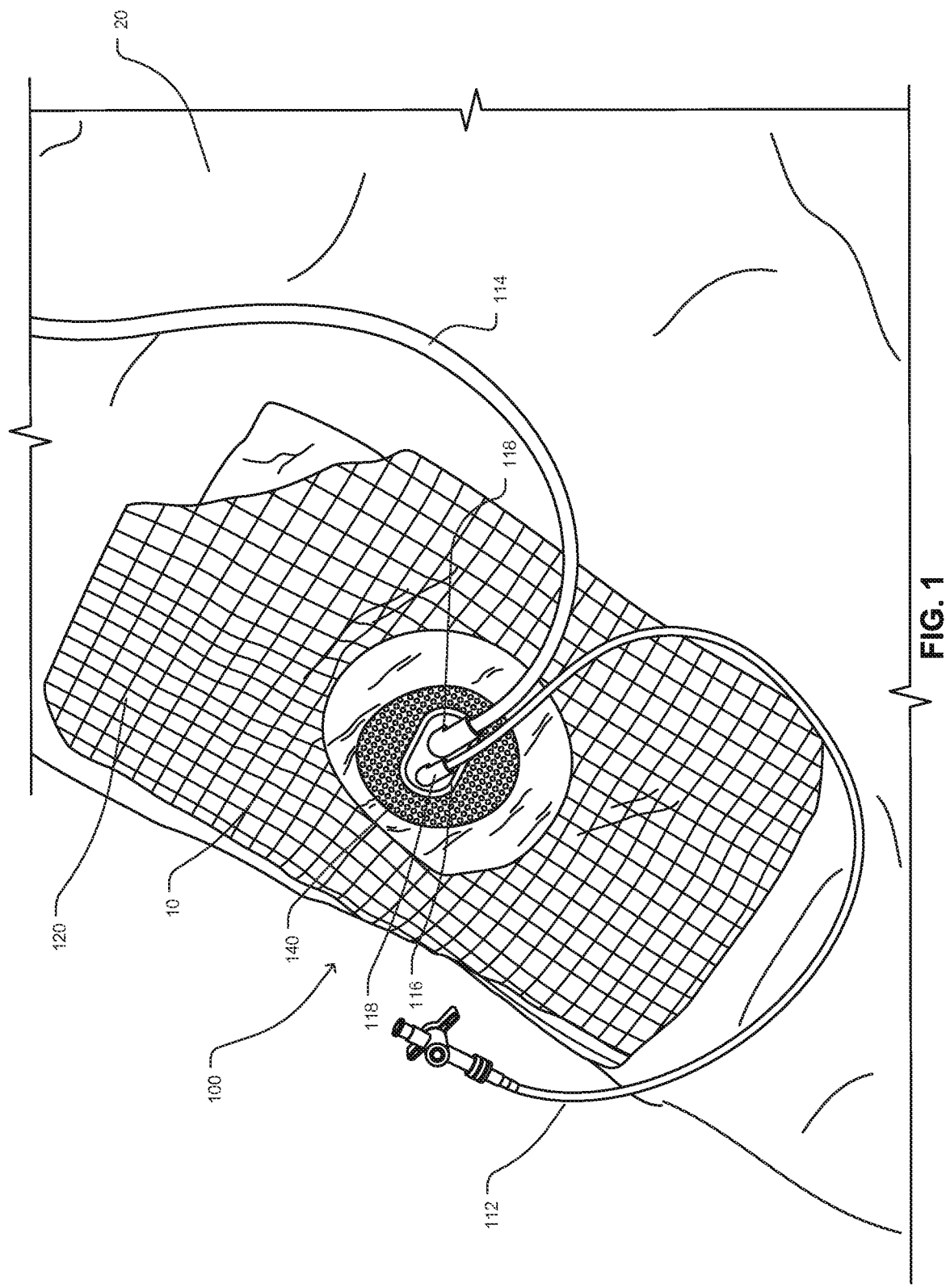
FIG. 1 is a perspective view of a first example of a multilayered dressing system sealed over a wound, in accordance with some embodiments.

Referring to FIG. 1, some embodiments of a system 100 can provide a unified dressing assembly ("UDA") for negative-pressure wound therapy (NPWT) (which can also be referred to as sub-atmospheric wound therapy) to facilitate healing and treatment of a sealed wound 10 of a patient 20. As described further below (e.g., refer to FIG. 2), the depicted embodiment of the system 100 includes a system arrangement, in which the various components used for sealing, dressing, suctioning and irrigating the wound 10 are coupled together as a single, composite unit such that no assembly of these components is required by the practitioner working to treat the wound. The system 100 may be used, for example, to quickly seal the wound area 10 by reducing the likelihood or eliminating the assembly of separate components for NPWT. In some embodiments, the system 100 can be used to apply a negative pressure (e.g., sub-atmospheric pressure) to the sealed wound 10 by connecting an outflow line (e.g., a negative pressure line 114) to a vacuum port of a manifold 118 for removal of effluent accumulating in the wound region 10 during the healing process. The system 100 can also optionally irrigate the wound 10 by connecting an inflow line (e.g., an irrigant supply line 112) to an irrigation port of the manifold 118 and delivering a fluid (for example, on an intermittent basis), such as saline solution or a therapeutic agent, to the periphery of the wound 10 rather than the superficial layers of a dressing, for example, by the use of an irrigation network (described in more detail below in connection with FIGS. 2, 3A-3B, and 4A-4D) that extends a plurality of tubes to periphery portions of the wound.

The depicted system 100 can include, in this particular embodiment, unified dressing elements that include a sealing layer 120, netting layers 140, and at least one port (e.g., vacuum port of manifold 118) for vacuum suction. The system 100 can also optionally include one or more irrigation networks 130 (best shown in FIGS. 2 and 4A-4D) and at least one ancillary port (e.g., irrigation port of manifold 118) for delivering an irrigant to the irrigation network(s). In various embodiments, elements of the system 100 can be provided in a variety of different sizes and shapes for sealing and filling the wound cavity 10. In some implementations, the system 100 can be made available in one or more portions that can be readily assembled, disassembled, or adjusted in size during a medical wound treatment procedure.

Figure 2:
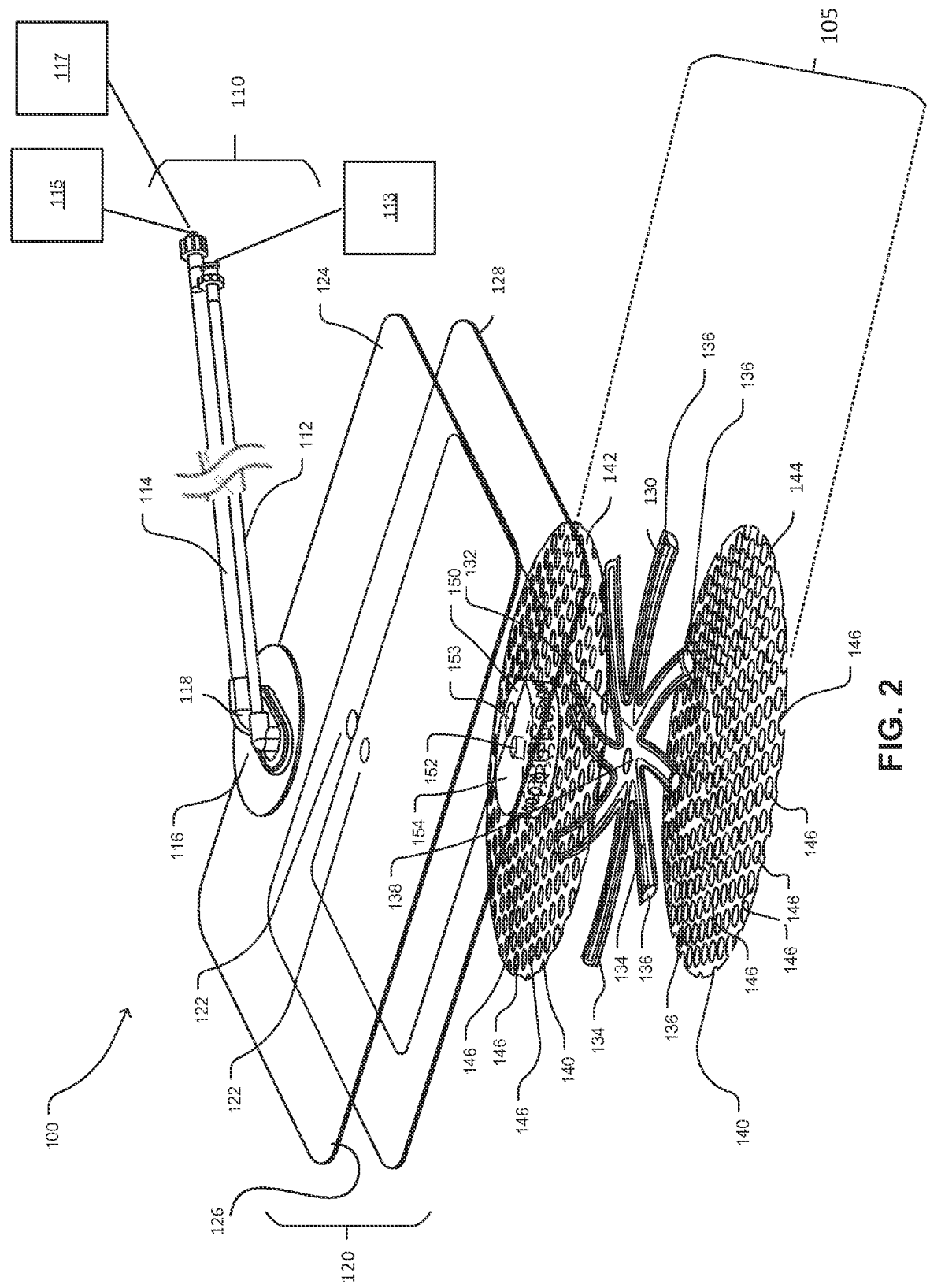
FIG. 2 is an exploded perspective view of the system of FIG. 1.

Referring to FIG. 2, certain embodiments of the system 100 can include a port assembly 110, a sealing layer 120, an irrigation network 130, and netting layers 140. The depicted system 100 includes a system having an inflow line 112 (e.g., an irrigant supply line 112) and an outflow line 114 (e.g., a negative pressure line 114) that provide fluid pathways into and out of a sealed wound (e.g., wound 10 of FIG. 1) through the manifold 118. In some embodiments, the system 100 can include a system 100 that includes the port assembly 110, the sealing layer 120, the irrigation network 130, and the netting layers 140 that are indirectly or directly fixedly attached in a pre-assembled form. In other embodiments, the system 100 can include two or more fixedly coupled elements in a pre-assembled form that can be quickly connected together with other elements of the system 100 such that minimal assembly by a practitioner is necessary when applying the system 100 during a medical procedure.

In this embodiment, the port assembly 110 includes a hub (e.g., a central hub 116) having a manifold 118 with two ports that can be connected to the inflow line (e.g., an irrigant supply line 112) and the outflow line (e.g., a negative pressure line 114). The hub 116 can be positioned on the sealing layer 120, exterior to the sealed wound, for aligning and connecting the inflow and outflow lines to openings 122 in the sealing layer 120. In some embodiments, the manifold 118 of the hub 116 can connect to the irrigant supply line 112, which provides a first fluid pathway from an irrigation fluid source 113 to the port assembly 110. In certain implementations, the manifold 118 of the hub 116 can connect to the negative pressure line 114, which provides a second fluid pathway from the port assembly 110 to a fluid collection container 115 and a vacuum source 117. The first fluid pathway can be used to deliver medicinal or antiseptic irrigation fluids and the second fluid pathway can be used to collect effluent and irrigant solution from the wound. In some embodiments, the inflow line may be a fluid delivering tubing that delivers irrigation fluid, such as saline solution or medicaments, to the wound and the outflow line may be a vacuum connection tubing that delivers wound fluid from the sealed portion of the wound to the collection container 115. As best seen in FIGS. 1 and 2, in some embodiments, the hub 116 is positioned centrally on the sealing layer 120 of the system 100. In some embodiments, the port assembly 110 can include multiple hubs for connecting one or more inflow and/or outflow lines with the system 100. Certain embodiments can include one or more hubs positioned at non-central, peripheral locations on the sealing layer 120. For example, some implementations of the system 100 may include a port assembly 110 that includes multiple inflow and outflow lines with separate hubs in various locations along the sealing layer.

Still referring to FIG. 2, the sealing layer 120 can include a film barrier 124 having a clear adhesive (e.g., a first sealing layer) on a central region of a wound-facing surface 126 of the barrier and an optional gel adhesive 128 (e.g., a second sealing layer) at peripheral locations on the wound-facing surface 126. In some implementations, the film barrier 124 can be a transparent plastic film, for example, a polyurethane film, that allows a practitioner to visually monitor the surface of a wound (e.g., wound 10 of FIG. 1) after the system 100 has been sealed over the wound. The film barrier 124 can be a liquid and air impermeable barrier, in some embodiments, to provide an air-tight or substantially air-tight seal for negative pressure therapy. In some implementations, the gel adhesive 128 can releasably bond the system 100 along the outer peripheral locations of the sealing layer 120 to skin, preferably undamaged skin, located around the wound. Certain embodiments of the gel adhesive 128 can be pulled from the skin and re-adhered to the skin such that the sealing layer 120 can be easily re-positioned, as desired. In some embodiments, the sealing layer can include a film barrier with a gel adhesive on the entire wound-facing surface. In some cases, additional agents such as medications and growth chemicals, can be embedded in the sealing layer to provide sustained release of medication, promote healing, or reduce the risk of infection of the wound.

The irrigation network 130 can include a body portion 132 (e.g., a central body portion) and eight outwardly radiating tubes 134 extending from the body portion 132. Each tube 134 is a hollow tubular member that defines a lumen 136 for providing a fluid connection with a cavity within the body portion 132 of the irrigation network 130. The irrigation network 130 can have a plurality of radiating tubes 134 for delivering an irrigant introduced through an aperture 138 defined by the body portion 132 to the periphery of the wound. In some embodiments, the irrigation network 130 can include two, three, four, five, six, seven, eight, nine, ten, or more than ten radiating tubes. The tubes 134 of the irrigation network 130 can have same or different lengths in relation to the body portion 132. In some embodiments, the irrigation network 130 can include an off-center (i.e., non-central) body portion having a plurality of radiating tubes 134 of varying lengths in relation to the body portion. Certain embodiments of the irrigation network 130 can include optionally one or more tubes 134 or a body portion 132 defining a plurality of apertures (not shown) for delivering an irrigant at or near central regions of the system 100.

In various embodiments, the radiating tubes 134 can deliver an irrigant to the periphery of the wound. The radiation tubes 134 can ensure that an irrigant is delivered across a wound surface by delivering the irrigant to the periphery of the wound and suctioning the irrigant to a center portion of the dressing, e.g., a centered suction port. As such, the radiating tubes 134 can provide the advantage of delivering an irrigant across a substantial portion of a wound surface. In some cases, the radiating tubes 134 are disposed at the wound surface, or positioned within about 1 mm to about 5 mm from the wound surface such that the irrigant contacts the wound as it proceeds centrally to the suction port. By delivering the irrigant to the periphery, the dressing can be configured to be cut to size or customized without losing the ability to irrigate.

Certain embodiments a system 100 can include suction ports at the peripheral location of the dressing and at least one irrigation port at a central location of the dressing to deliver an irrigant across a wound surface. In some embodiments, a system 100 may use radiating tubes 134 for a suctioning effect and a central irrigation port for delivering an irrigant.

Still referring to FIG. 2, the depicted netting layers 140 include a dorsal perforated layer 142 (e.g., first perforated layer) and a ventral perforated layer 144 (e.g., a second perforated layer). "Netting" is a material with holes, or spaces, that allow fluids and gasses to pass through the netting. The term "netting" is a broader term than the terms perforated layer or mesh layer. Netting in the present context encompasses the perforated or mesh layers—that is, all types of perforated or mesh materials are netting, but certain types of netting materials, such as the perforated layers, are not considered meshes.

In some embodiments, the dorsal and ventral perforated layers 142, 144 are positioned above (i.e., superior) and below (i.e., inferior), respectively, to the irrigation network 130 of the system 100. The netting layers 140 can be positioned between other elements of the system 100, for example, as shown in the depicted embodiment, the dorsal perforated layer 142 can be positioned between the sealing layer 120 and the irrigation network 130 to reduce the likelihood or prevent wound tissue from clogging a vacuum flow path. In certain implementations, at least a portion of the netting layers 140 is the most inferior component of the integrated system 100 that directly contacts and rests on a surface of the wound tissue. For example, the depicted ventral perforated layer 144 of FIG. 1 is positioned inferior to the irrigation network 130 and disposed on the wound surface, and is therefore sometimes referred to as a contact layer. In various implementations, the netting layers 140 can facilitate irrigation and debridement of the wound tissue by allowing fluids to travel through pores 146 of the perforated layer. Certain embodiments of the netting layers, e.g., the dorsal perforated layer 142, can assist with distributing negative pressure that might otherwise accumulate within the sealed portion of the system 100, in addition to evacuating exudates and irrigants from a sealed wound area. In some embodiments, the netting layers 140 that directly contact tissue, e.g., the ventral perforated layer 144 (or contact layer), can be adapted to prevent tissue ingrowth. In some embodiments, the netting layers 140 can include one or more than two perforated layers, for example, three, four, five, six, seven, eight, nine, ten, or more than ten perforated layers. As will be discussed in greater detail below, various implementations of the netting layers 140 can include non-woven layers such as the perforated layers or meshes having randomly oriented fibers. Other implementations of netting layers 140 can also include woven layers and knitted layers.

Figure 3A:
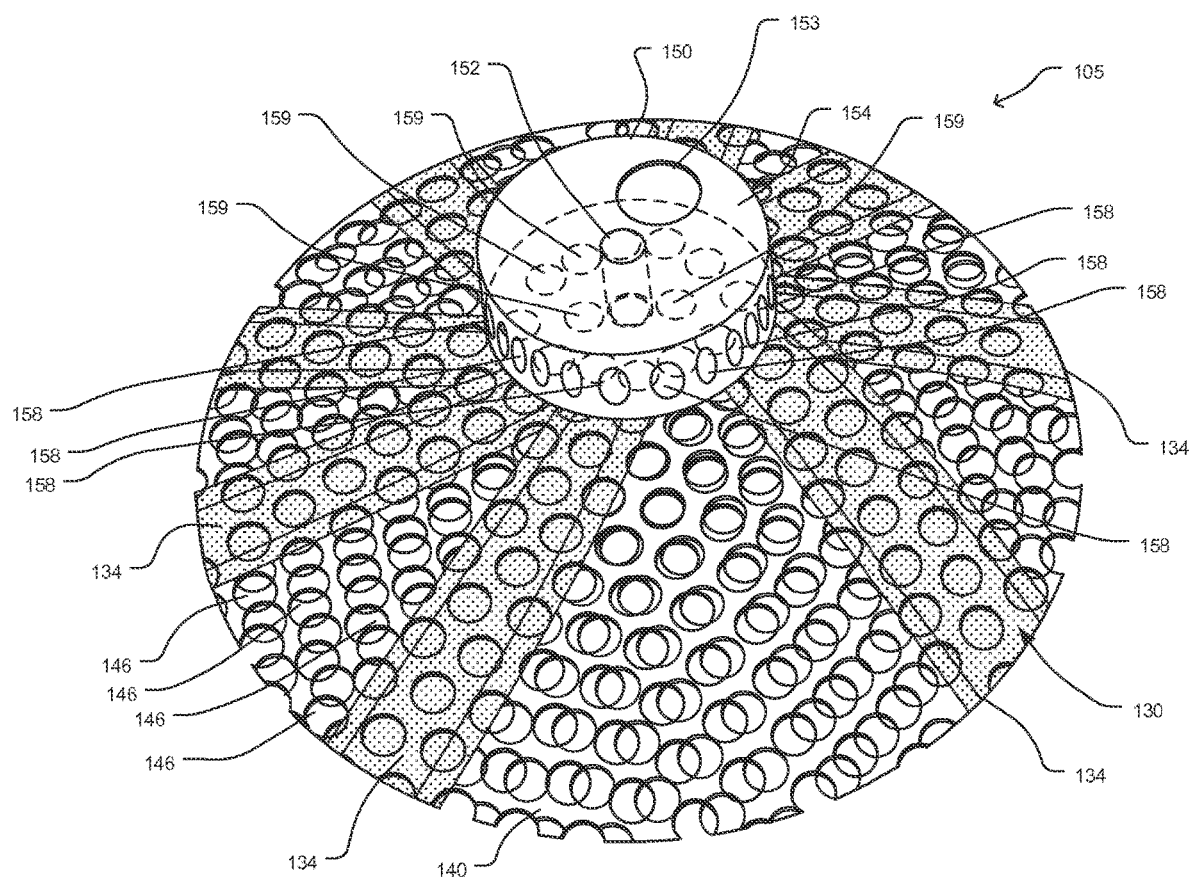
FIGS. 3A and 3B are a perspective view and a side view of sealed portions (e.g., an irrigation network, netting layers and a vacuum interface chamber) of the system of FIG. 1. The side view shown in FIG. 3B provides a cutaway view of the vacuum interface chamber.
Figure 3B:
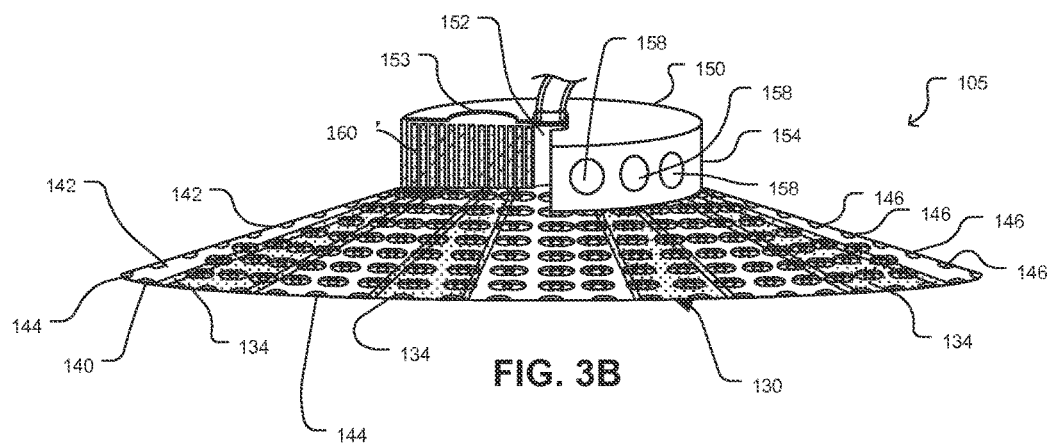

Referring to FIGS. 2, 3A and 3B, the system 100 may optionally include a vacuum interface chamber 150 disposed between the sealing layer 120 and a perforated layer, e.g., the dorsal perforated layer 142, to distribute negative pressure within the sealed portion of the system 100. The depicted vacuum interface chamber 150 of FIG. 2 includes a central lumen 152 for delivering an irrigant to the irrigation network 130 and an inlet opening 153 for suctioning fluids to a fluid collection chamber 115. In some implementations, the vacuum interface chamber 150 can have a body 154 that is disk-shaped or cylindrical and defines a plurality of pores 158, 159. For example, the depicted vacuum interface chamber 150 includes a disk-shaped body 154 having a side wall with side pores 158 and a floor with ventral pores 159 to allow the passage of fluid therethrough toward the port assembly 110 and, ultimately, the fluid collection chamber 115. As will be discussed in greater detail below with FIGS. 3A and 3B, certain implementations of the vacuum interface chamber 150 can include an interior cavity with a series of ridges 160 (see FIG. 3B), walls or other structural components that distribute negative pressure from the central suction tube insertion point to a plurality of channels.

In use, vacuum suction flow of the system 100 can be distributed by the plurality of channels of the vacuum interface chamber into a plurality of suction flow paths positioned on a dorsal surface of the dorsal perforated layer 142. As will be discussed further with FIGS. 9A-9B and 10A-10B, a plurality of suction flow paths can pull fluids transversely through the netting layers 140 through the pores of the perforated layers or laterally through a gap between the perforated layers.

In some embodiments, other types of structures may be contemplated for distributing vacuum suction through the system 100. In certain implementations, the integrated system 100 can include a central suction flow path that is distributed through the use of multiple vacuum channels and/or vacuum interface chambers.

Referring to FIGS. 3A and 3B, sealed portions of the system 100 of FIG. 2 (i.e., elements 105 disposed inferior to a sealing layer, e.g., the sealing layer 120 of FIG. 2) can include the irrigation network 130 and the netting layers 140. The irrigation network 130 can be disposed between netting layers 140 of the system, for example, between two perforated layers such as the dorsal perforated layer 142 and the ventral perforated layer 144 (best shown in FIG. 2). The irrigation network 130 can have a fluid connection channel that extends from a manifold (e.g., the manifold 118 of FIG. 2) to the vacuum interface chamber 150. Irrigation fluids can be delivered to the peripheral wound areas when transported through the central lumen 152 of the vacuum interface chamber 150 to an inlet aperture 139 (see FIG. 4A) of the irrigation network 130 for irrigant dispersion at open ends of the radiating tubes 134. As will be discussed further below, the vacuum interface chamber 150 includes the opening 153 for distributing vacuum suction flow to a plurality of channels 160 (see FIG. 3B) within the vacuum interface chamber 150.

Referring to FIGS. 3A and 3B, the netting layers 140 include the dorsal perforated layer 142 and the ventral perforated layer 144. In some embodiments, the dorsal and ventral perforated layers 142, 144 can be flexible, thin layers that each comprise a plurality of pores 146 (or an array of apertures) therethrough that allow for the removal of fluids (e.g., exudate and irrigant) from the sealed wound area and the distribution of vacuum suction within the sealed wound cavity (e.g., the wound 10 of FIG. 1). The perforated layer thickness, material characteristics, and pore size and density may be adjusted, as desired, to form a suitable netting layer. In some embodiments, the thickness of the layers can be range from about 0.5 mm to about 5 mm. The length and width of the layers can each range from about 10 centimeters (cm) to about 100 cm. Pore sizes of the layers are discussed in sections below.

The dorsal and ventral perforated layers 142, 144 can include circular-shaped pores 146, as shown in FIGS. 2, 3A and 3B. Each perforated layer 142, 144 can include pores 146 shaped to facilitate a desired function, for example, pores 146 having a shape with an increased number of corners, e.g., a star, because it may be desirable for the ventral perforated layer 144 to contact and roughen the wound surface in certain implementations. Suitable pore shapes of the perforated layers 142, 144 include, but are not limited to, oval or polygonal shapes, such as rectangular, triangular, pentagonal, octagonal, star, or square shapes (as shown in FIGS. 9A and 9B). For example, some embodiments of the perforated layers 142, 144 include pentagonal pore shapes that form a honeycomb shaped structure. In some embodiments, at least two of the perforated layers 142, 144 can include different pore shapes to reduce the likelihood or prevent the perforated layers 142, 144 from aligning with one another to produce an appropriate amount of turbulence flow through the netting layers 140. In particular, certain implementations of the perforated layers 142, 144 can include alternating pore shapes in consecutive layers to encourage horizontal fluid flow through the netting layers 140.

In some implementations, perforated layers 142, 144 of the netting layers can be positioned such that pores 146 of each perforated layer 142, 144 are positioned in an offsetting manner to facilitate a more uniform distribution of vacuum suction along the sealed wound. For example, the pores of one layer, e.g., the dorsal perforated layer can be positioned to stagger a position of the pores of the dorsal layer relative to a position of the pores of the ventral perforated layer. In some embodiments, the perforated layers can be oriented such that the position of the pores of each layer are aligned, thus eliminating an offset, to facilitate increased transverse fluid flow through the perforated layers. Some implementations of the netting layers 140 include creating a rotational offset between at least two perforated layers 142, 144 such that the pores of two consecutive layers do not align with one another. For instance, the dorsal perforated layer 142 may be rotated about a central axis that extends through the central lumen 152 of the chamber interface 150 between about 5 degrees and about 45 degrees to create a rotational offset between the pores of the dorsal and ventral perforated layers 142, 144. Alternatively, in some embodiments, at least two consecutive perforated layers can include same or similar shaped pores to facilitate vertically-oriented flow through at least a portion of the netting layers 140. In some cases, the pore of the layers 142, 144 may vary in size and/or shape between perforated sheets. For example, some layers may include pores that form a screen, radial webbing, honeycombed structure, or other pore configuration, to encourage vertical flow through the system 100 while, in some cases, also preventing tissue ingrowth.

Still referring to FIGS. 3A and 3B, some embodiments of the netting layers 140 include perforated layers 142, 144 with pore configurations having a regular pattern such as a uniformly perforated pattern (e.g., perforated layers 142, 144) or a screen-like pattern (best shown in FIGS. 9A and 9B), variable patterns such as a radial or spider web pattern, random patterns, or a combination thereof. The pores 146 of the netting layers 140 can be sized, as desired, for evacuating fluids and distributing negative pressure. Some implementations of the netting layers 140 can include pores 146 having a uniform size while other implementations include netting layers 140 include varying sizes of pores. For example, each pore 146 can include a dimension (e.g., a diameter, length or width) that can range from about 0.5 millimeters (mm) to about 10 mm (e.g., from about 0.5 mm to about 1 mm, from about 1 mm to about 2 mm, from about 2 mm to about 3 mm, from about 3 mm to about 4 mm, from about 4 mm to about 5 mm, from about 5 mm to about 7 mm, or from about 7 mm to about 10 mm). Some implementations of the netting layers include pores 146 sized to prevent tissue ingrowth into the perforated layers 142, 144.

Certain embodiments of the netting layers, such as the perforated layers, can be made by cutting, e.g., cutting die, a desired layer shape from a thin solid sheet of a material and perforating holes into the layer using, for example, a laser.

Still referring to FIGS. 3A and 3B, the netting layers 140 can optionally include the vacuum interface chamber 150, which has the opening 153 having fluidic communication with the outflow line (e.g., a negative pressure line 114 of FIG. 2) leading to a regulated vacuum source (e.g., the vacuum source 117 of FIG. 1). Effluent can be suctioned from the sealed portion of the wound through the vacuum interface chamber 150 to the collection canister (e.g., the canister 115 of FIG. 1) via the outflow line (e.g., a negative pressure line 114 of FIG. 2). The vacuum interface chamber 150 is typically made from a soft medical grade plastic (e.g. Silastic) that encloses a specified volume of space within a predetermined height and circumference of the plastic walls, e.g., 2 cc to 50 cc. The end result is a closed cell with one or more access ports and perforations. In at least one embodiment there is one main port on the dorsal surface (the single perforation in the dorsal surface of the chamber), which is a line or tubing connection point for the vacuum circuit. There are typically a number of perforations in the vacuum interface chamber 150 on the ventral (wound facing) surface and sometimes on the side surfaces, as well for providing multiple vacuum flow paths within the sealed portion of the system and preventing the vacuum flow blockage that might be caused by the wound becoming suctioned to a limited number of vacuum flow paths.

Referring to FIG. 3B, vacuum interface chamber 150 includes multiple vacuum flow paths created by the internal risers and perforations in the peripheral (or lateral) wall and ventral wall of the chamber. Some embodiments disclosed herein feature a vacuum interface chamber that serves as a communication point between the vacuum source and effluent exiting the dressing. The chamber can be a relatively thin walled, flexible closed cell, with internal risers to keep the walls of the chamber from collapsing on each other when negative pressure is applied. The material the chamber is constructed out of may be plastic, rubber, metal or polymer. The diameter of the chamber may range from less than 1 cm to about 3 cm in diameter and less than 1 cm to about 1 cm in height. The size may vary based on the size of the dressing. The risers may be from <1-3 mm in thickness to resist chamber compression. The ventral (facing the wound) side and peripheral (lateral) wall have multiple perforations to communicate the vacuum entering the dressing across the dimensions of the wound sealed under the dressing. This embodiment resembles a shower head, but in reverse, that is, a showerhead that projects water ante grade. This embodiment describes the retrograde flow-path for the vacuum and evacuated effluent. There is a central vacuum source connection opening that communicates with a central cavity in the vacuum interface chamber in an airtight fashion, with a multitude of vacuum flow-paths created by the internal risers and perforations, which "showers" vacuum onto the sealed wound. Alternatively, the chamber can be composed of a solid piece of medical grade polymer with a multitude of internal pathways that come to a central point that is in communication with the vacuum source. The internal pathways are separated from each other by the medical grade polymer, which serves to add structure to the chamber and maintain a specified spatial orientation of the pathways. Lastly, the walls of the vacuum interface chamber can be thick enough and constructed of material that prevents collapse of the internal space of the vacuum interface chamber. Either of these two embodiments obviates the need for internal risers/bosses to keep the central cavity/chamber open.

Figure 3C:
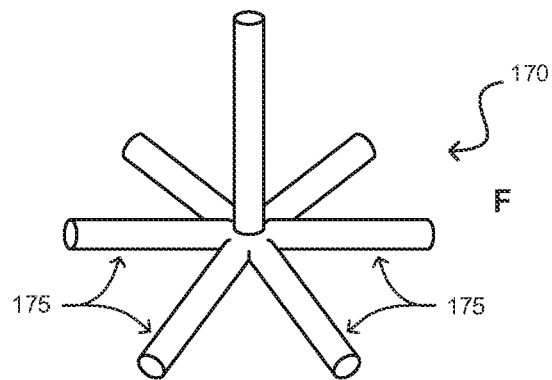
FIGS. 3C-3E are perspective views of alternative embodiments of a multi-flanged design for delivering suction to a sealed portion of systems provided herein.
Figure 3D:
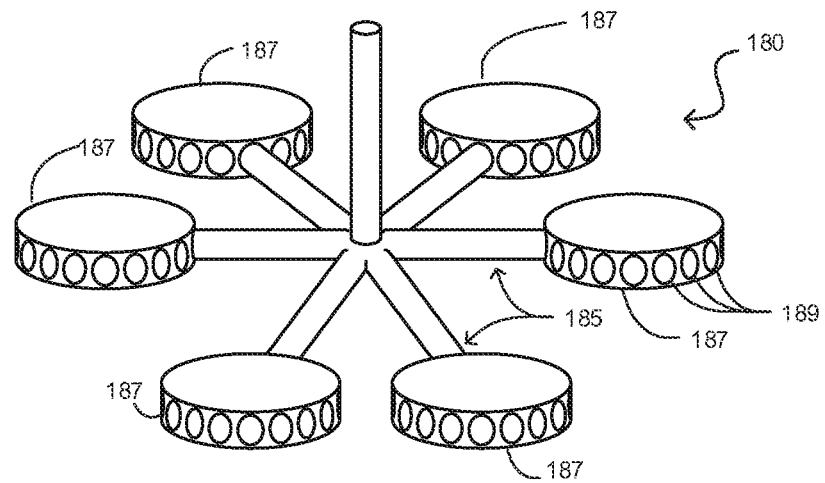
Figure 3E:
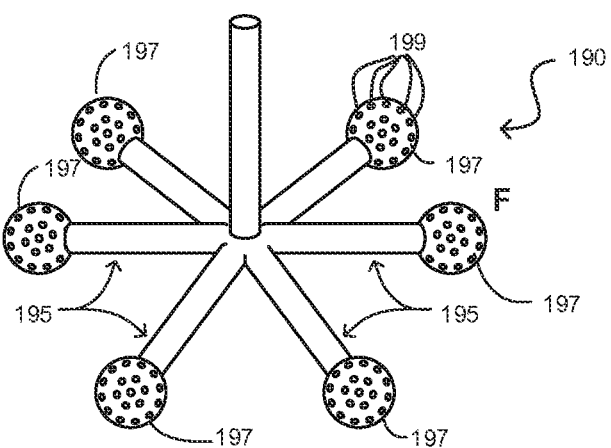

Referring to FIGS. 3C-3E, other embodiments of systems 100 have a vacuum flange interface 170, 180, 190 rather than a single vacuum interface chamber (e.g., the vacuum interface chamber 150 of FIGS. 3A and 3B). The flange interface 170, 180, 190 is devoid of a single deep surface (e.g., ventral side or floor), and acts as a docking port for the outflow line (e.g., a negative pressure line 114) to communicate with the sealed dressing. In the flange interface 170, 180, 190 embodiments, the area under the sealed dressing is considered a single closed space, and generally has equal pressure at all points. The single vacuum pathway in the flange is the sole source of vacuum entering the dressing and the sole path for effluent to exit the dressing. In some embodiments, a multi-flange system 170, 180, 190 can include a number of flanges 175, 185, 195 arrayed in a radial pattern that allows many sources of suction. In certain embodiments, the flange can be the integrated fixation point for a negative pressure line 114, or a vacuum tubing system, to the dressing. In some embodiments, as shown in FIGS. 3C-3D, the system 100 can include a multi-flange design 170, 180, 190 for delivering suction to the sealed portion of the system 100, such that several flanges 175, 185, 195 are aligned along a same transverse plane and each flange 175, 185, 195 provides equal suction force through the sealed portion of the integrated system. The multi-flange design 170, 180, 190 would allow for continued suction through the system 100 even if one flange became clogged since there would be several other remaining flanges to continue providing suctioning. Referring to FIG. 3C, in some embodiments, the system 100 can include a multi-flange design 170 having several flanges 175 that each provide a single lumen for delivering suction. Some embodiments include a multi-flange design 180 with a plurality of flanges 185 in which each flange includes a disk-shaped vacuum interface chamber 187 disposed at the terminal end for distributing suction through a series of apertures 189 disposed along the sides and ventral side or floor (not shown) of the vacuum interface chamber 187. As shown in FIG. 3E, in some implementations, the multi-flange design 190 can include flanges 195 having spherical shaped vacuum interface chambers 197 defining a plurality of apertures 199.

In certain implementations, the system 100 can include a separating layer between the irrigation network and at least one of the perforated layers of the netting layers to promote dispersion of an irrigant delivered at the wound surface to the peripheral wound area. In particular, the separating layer can be placed between the irrigation network and a perforated layer positioned superficial to the irrigation network, e.g., the dorsal perforated layer. The separating layer can provide a barrier that forces the irrigant to flow from a central portion of the wound dressing to the peripheral portions of the wound dressing before flowing back toward the suction manifold port positioned at the hub.

Referring to FIGS. 4A-4C, the irrigation network 130 of FIG. 2 includes the aperture 138 in fluid connection with the irrigant manifold 118 supplying an irrigant. The irrigation network 130 can include the plurality of tubes 134 that radiate outwardly from the aperture 138. The irrigation network 130 can be made of a compliant material that allows the tubes to have expandable or collapsible lumens 136, depending on pressure within the irrigation network 130. Collapsible lumens provide a compliant design for reducing wound irritation that might be otherwise caused by a hard, non-compliant tubing that places increased pressures on the wound. Compliant tubes are, in some cases, capable of folding on itself and therefore do not create high stress points on the wound surface. In various embodiments, the compliant tubing can be mechanically assembled in manufacturing and therefore do not need to be assembled during its application. For example, the lumens 136 can expand into an open configuration when the tubes are subjected to positive pressure and partially or fully collapse into a closed configuration when the tubes are subjected to zero or negative pressure. Referring to FIG. 4B, the flow of an irrigant can create positive pressure that expands the lumens of the tubes 134. When there is low or no flow of irrigants, the tubes can collapse partially, as shown in FIG. 4C, or collapse completely, as shown in FIG. 4D. Suitable irrigation network materials can include, but are not limited to, elastomeric polymers, such as silicone. The tubes 134 described herein can provide the benefit of providing a flexible irrigation structure that can conform to unique wound sizes as well as reduce the likelihood or prevent tissue irritation of the wound.

In some embodiments, each tube 134 of the irrigation network 130 includes two sealed edges that can optionally extend outwardly away from the lumen, which is best shown in FIGS. 4B and 4C. In some implementations, the sealed edges of the irrigation network can provide an attachment area for coupling the irrigation network to another portion of the system, for example, the perforated layers of FIGS. 3A and 3B.

In use, the irrigant manifold port supplies an irrigant to the irrigation network. The irrigant is introduced into the irrigation network through the aperture 138 and flows out the lumen ends of the tubes 134, supplying the peripheral edge of the wound with the irrigant. The manifold of the port assembly is positioned on the top dressing to suction the effluent and excess irrigant from the peripheral edges of the wound back towards the manifold at the central region of the system 100 and, subsequently, to the fluid collection container 115.

In some embodiments, the system 100 can include multiple irrigation networks. For example, some implementations of the system can include two irrigation networks, for example, a dorsal (e.g., a first irrigation network) and a ventral irrigation network (e.g., a second irrigation network). In some cases, there can be branching of the radiating tubes to allow more wide coverage with larger dressings. In some embodiments, multiple irrigation networks may be positioned adjacent to one another. Alternatively, in other embodiments, one or more perforated layers or vacuum interface chambers may be disposed between multiple irrigation networks, for instance, a ventral perforated layer can be placed between the dorsal and ventral irrigation networks.

Figure 5A:
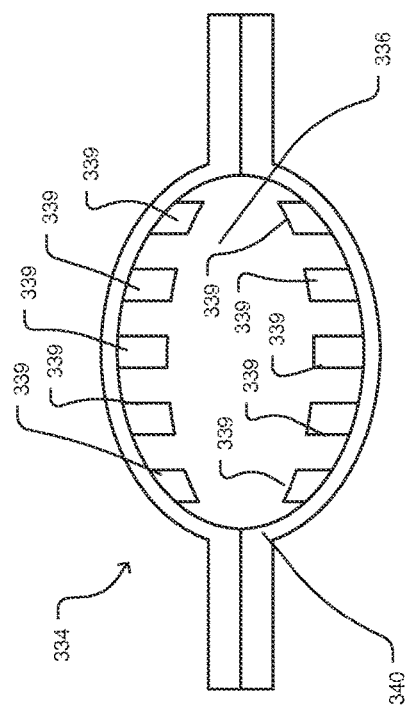
FIGS. 5A and 5B are cross-sectional views of another example of an irrigation network shown in an open and closed state, respectively.
Figure 5B:
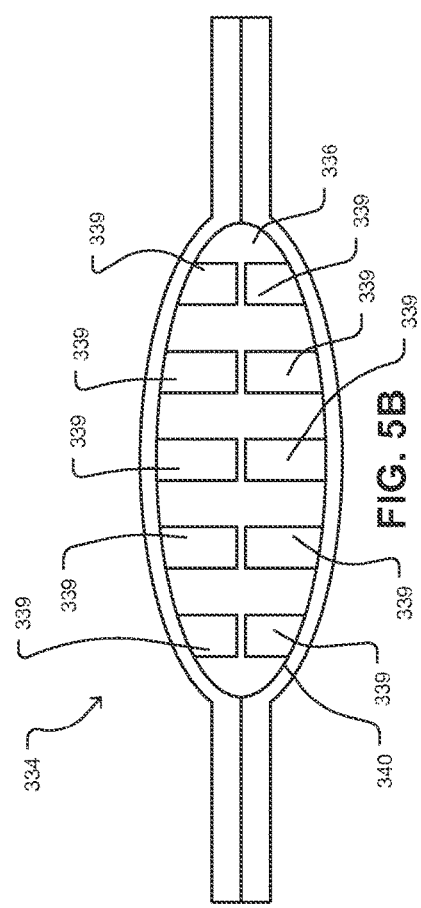

Referring to FIGS. 5A and 5B, tubes of a second example of a tube 334 of an irrigation network (e.g., irrigation network of FIGS. 4A-4C) that includes one or more protrusions 339 along at least a portion of a luminal wall 340 of a lumen 336 of the tube 334 to maintain patency of the flow paths within the irrigation network 330. In various embodiments, the protrusions 339 can prevent full closure of the lumen 336 of the tube 334 in a zero or negative pressure condition. In some embodiments, the protrusions 339 can be randomly oriented or aligned in a pattern along the luminal wall 340 of the tube 334. Each protrusion 339 can have a variety of different shapes, such as a protuberance (e.g., a nub or bulge) or elongate extensions (e.g., cilia or fingers). In some implementations, the tube 334 can include a luminal wall 340 with non-uniform or textured surfaces that prevents complete closure (or full collapse) of the tube lumen 340 in a zero or negative pressure condition. Fluidity between the protrusions 339 within one or more tubes 334 of the irrigation network allows irrigation to pass through from a manifold (e.g., manifold 118 of FIG. 2) to the outer periphery of the wound (e.g., wound 10 of FIG. 1).

Figure 6:
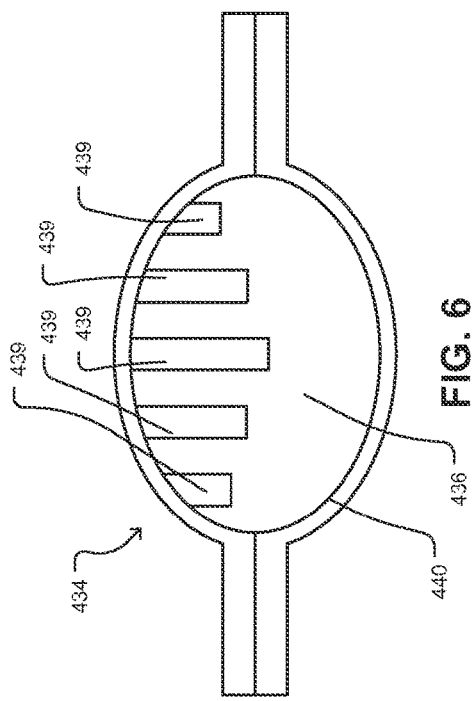
FIG. 6 is a cross-sectional view of yet another example of an irrigation network shown in an open state.

Referring to FIG. 6, yet another exemplary tube 434 can include protrusions extending radially inward from an inner wall 440 to provide flow path patency. Certain implementations of the radiating tubes 434 can include protrusions 439 that are located fully circumferentially along the inner walls of the lumens 436. For example, as shown, the tube 434 may include protrusions 439 along a top portion or a bottom portion of the lumen 436. In other implementations, as shown in FIGS. 5A and 5B, the protrusions 439 can be positioned along the entire circumference of the lumen.

Referring to FIGS. 7A and 7B, a method of fabricating the irrigation network 130 of FIGS. 4A-4C includes forming two desired irrigation patterns 131 (e.g., a first and a second pattern) from two flat sheets of a material and joining the irrigation patterns 131 together. Each pattern 131 can be formed from a flat sheet by cutting, e.g., die cutting in manufacturing, a desired shape from the flat sheet. The irrigation patterns 131 may be adjoined along an outer perimeter seam, with exception of lumen ends 135 of the irrigation network 130.

The top and bottom patterns 131 can be made from various sheets of materials that include, but are not limited to, thermoplastic, thermoset and elastomeric polymeric materials. Certain embodiments can include sheets made of silicone or polyurethane.

Referring to FIGS. 8A-8C, a method of fabricating the exemplary irrigation network that includes a plurality of tubes having protrusions 339 (e.g., the tube 334 of FIGS. 5A and 5B) includes affixing the outer perimeter seams 333 of two irrigation patterns 331 (e.g., a first and a second pattern) together, with exception of leaving open lumen ends 335. In some embodiments, each pattern 331 can be formed by cutting a desired shape from a sheet having one flat face and one textured face including a plurality of protrusions 339 described herein. The patterns 331 are brought together such that the textured sides of each pattern 331 are facing one another. Each pattern 331 can include a textured side that includes protrusions 339 such that lumens 336 of the irrigation network remain partially open in a zero or negative pressure condition, for example, in conditions where no fluids are being flushed through the irrigation network. The textured side can include a seam, i.e., a non-textured portion along an outer perimeter of each radiating tube 334, to facilitate as a bonding site for each sheet. The sheets are brought together and bonded along non-textured seams 333 as shown in FIG. 8B. The resulting irrigation network includes tubes having partially collapsible lumens 336 as shown in FIG. 8C.

In some embodiments, the outer wall of the radiating tubes can have bumps or raised texture to allow for a suctioning fluid pathway within the dressing. For example, radiating tubes can include bumps (or protrusions) on both sides of each sheet that make up the tubes to facilitate irrigant flow around the radiating tubes as an irrigant travels from the periphery of a wound to a central suction port of the system.

Referring back to FIG. 6, in some embodiments, the irrigation network can be formed by joining one irrigation pattern (e.g., the first pattern) that has a textured face and one irrigation pattern (e.g., the second pattern) having a non-textured flat surface, such as the tube 434 of FIG. 6. In such embodiments, the first pattern includes a textured side having protrusions 439 that contact the flat surface of the second pattern such that lumen 436 of the tube 434 remain partially open in a zero or negative pressure condition.

Referring to FIGS. 9A-9C, exemplary perforated layers 542, 544 of netting layers 540 of a system each have a plurality of square-shaped pores 546 that allow for fluid flow through the layers 542, 544. The netting layers 540 can include a first perforated layer 542 and a second perforated layer 544, each having pores 546 for allowing for debridement facilitated by vacuum suctioning of the system. The perforated layers 542, 544 can allow for vertical and horizontal (i.e., transverse) flow paths. The perforated layers 542, 544 of the netting layers 540 can be separated by a gap 548 in the system. The amount of separation created by the gap 548 can be dependent on a thickness of an irrigation network (e.g., the irrigation network 130 of FIG. 2). In some embodiments, the irrigation network thickness can fluctuate, depending on whether the lumens of the tubes are fully open, partially open or closed. As illustrated by FIG. 9B, effluent (e.g., dead, damaged or infected tissue and bodily fluids) can flow transversely through the gap 548 between the first and second perforated layers 542, 544 in a horizontal direction from one side of a perforated layer to an opposite second side of the perforated layer. The netting layers 540 allows for vertical fluid flow or both vertical and horizontal flow through the first and second perforated layers 542, 544 as shown in FIG. 9C.

Referring to FIGS. 10A and 10B, other types of netting layers include a mesh layer 640 having woven or knitted fibers 646 that permit fluid to flow through the layer 640. Certain embodiments of the system described herein can include at least one mesh layer 640 for assisting debridement during wound healing. The mesh layer 640, similar to a perforated layer (e.g., perforated layers 542, 544 of FIGS. 9A-9C), can allow for horizontal and vertical flow paths, as depicted by the arrows, through the mesh layer 640 to facilitate suctioning of effluent through the system. The mesh layer 640 can be made of a medical grade polymer such as a polyester, in some embodiments.

Some embodiments of the system can include a composite dressing having both perforated layers (e.g., perforated layers 542, 544 of FIGS. 9A-9C) and mesh layers. For example, an exemplary composite dressing may include a dorsal layer and a ventral perforated layer in which one or more intermediary mesh layers are placed therebetween.

The perforated layers (e.g., perforated layers 542, 544 of FIGS. 9A-9C) and/or mesh layers can be made of various materials. Each perforated (or mesh) layer can be made of various medical grade polymers. Suitable perforated (or mesh) layer materials include, but are not limited to, silicone and polyurethane. Other suitable materials can include, but are not limited to, cotton, polyester, rayon, acrylic, polypropylene, nylon, polyethylene and combinations thereof. Some embodiments of the system include perforated (or mesh) layers having same or different materials, for example, the ventral perforated layer may be made of silicone while the dorsal perforated layer is made of polyester, in some embodiments.

In certain implementations, one or more of the perforated (e.g., perforated layers 542, 544 of FIGS. 9A-9C) and/or mesh layers of the system may be made of biodegradable or bioresorbable materials, e.g., polylactide (PLA) or poly-L-lactide (PLLA). Other suitable polymers can include a resorbable polymer selected from the group consisting of poly(orthoester), polyanhydride, poly(phosphazene), poly-hydroxyalkanoate, polycarbonate, tyrosine polycarbonate, polyamide, polypeptide, poly(amino acid), polyesteramide, poly(alkylene alkylate), polyether, polyethylene glycol, polyethylene oxide, polyvinyl pyrrolidone, polyurethane, polyetherester, polyacetal, polycyanoacrylate, poly(oxyethylene)/poly(oxypropylene)copolymer, polyacetal, polyketal, polyphosphate, polyphosphoester, polyalkylene oxalate, polyalkylene succinate, poly(maleic acid), silk, recombinant silk, chitin, chitosan, polysaccharide, and polymers comprising glycolic acid, 1,4-dioxanone, trimethylene carbonate, 3-hydroxybutyric acid, 4-hydroxybutyrate, and β-caprolactone, including polyglycolic acid, polylactic acid, polydioxanone, polycaprolactone, copolymers of glycolic and lactic acids, polyacrylic acids, and poly(lactide-co-caprolactone). Certain implementations of the system may include biodegradable or bioresorbable layers for providing a dressing substrate and repairing damaged tissue, for example, such as replacing fascia defects of a wound. Benefits of using biodegradable or bioresorbable layers in the system can include reducing the risk of foreign body reactions or chronic infection in cutaneous and subcutaneous tissue following device use.

The system can include a ventral perforated layer such as the ventral perforated layer 144 of FIG. 2 (or optionally a mesh layer, e.g., the mesh layer 640 of FIG. 10A) that comes into contact with wound tissue that is configured to promote tissue ingrowth. For example, the ventral perforated layer may be composed of a synthetic skin matrix material, or a biodegradable or a bioresorbable material. The ventral layer can have pores sized to encourage tissue ingrowth. In some implementations, the ventral layer can be configured to separate from the rest of the system such that the ventral layer can remain in the patient's body while the remainder of the system is removed. The ventral layer can act as a tissue ingrowth barrier for other components of the system. In some embodiments, the ventral layer can include medications or chemicals that include, but are not limited to, growth factors, antibiotics and anti-inflammatory agents.

In some embodiments, a biodegradable or a bioresorbable perforated layer (e.g., perforated layers 542, 544 of FIGS. 9A-9C) and/or mesh layer (e.g., the mesh layer 640 of FIG. 10A) may allow the system to remain in a patient for a longer duration or permanently. In some implementations, the system can include one or more biodegradable or bioresorbable layers that may be left in a wound for greater than 48 hours, 72 hours, 96 hours, 120 hours, or greater than 120 hours. In some embodiments, a portion of the dressing layers can be disassembled from the system and remain in the patient, for example, a ventral layer of the netting layers can be disassembled and left within the wound.

Certain implementations of the biodegradable or bioresorbable perforated layer (e.g., perforated layers 542, 544 of FIGS. 9A-9C) and/or mesh layer (e.g., the mesh layer 640 of FIG. 10A) can include collagen or other biological materials, antibiotics, and/or growth factors to promote the growth of granulation tissue and tissue healing. The biological materials, antibotics and/or growth factors can be configured for immediate release and/or an extended release mechanism that occurs over a predetermined time frame as the biodegradable or bioresorbable polymer dissolves away within the wound. The biological materials, antibiotics and/or growth factors can be infused within the biodegradable or bioresorbable polymer to provide an extended release of substances. The biodegradable or bioresorbable layers can be composed of fibers, such as electrospun fibers, having a fiber diameter sized to approximate human tissue dimensions of about 1 micron. Some embodiments of the biodegradable or bioresorbable layers can include smaller pores sized to promote tissue ingrowth in addition to larger pores sized to allow for debridement.

Some embodiments of the perforated layers (e.g., perforated layers 542, 544 of FIGS. 9A-9C) and/or mesh layers (e.g., the mesh layer 640 of FIG. 10A) of the system can include a coating. For example, in some implementations, the layers can include a hydrophobic coating to seal the layer material and maintain the integrity of the layer. Other implementations can include a tissue interfacing coating that promotes or prevents tissue ingrowth. For example, petrolatum, a topical antibiotic application, and/or other lubricants may be applied to the dressing layers to prevent tissue ingrowth, as desired.

Figure 11A:
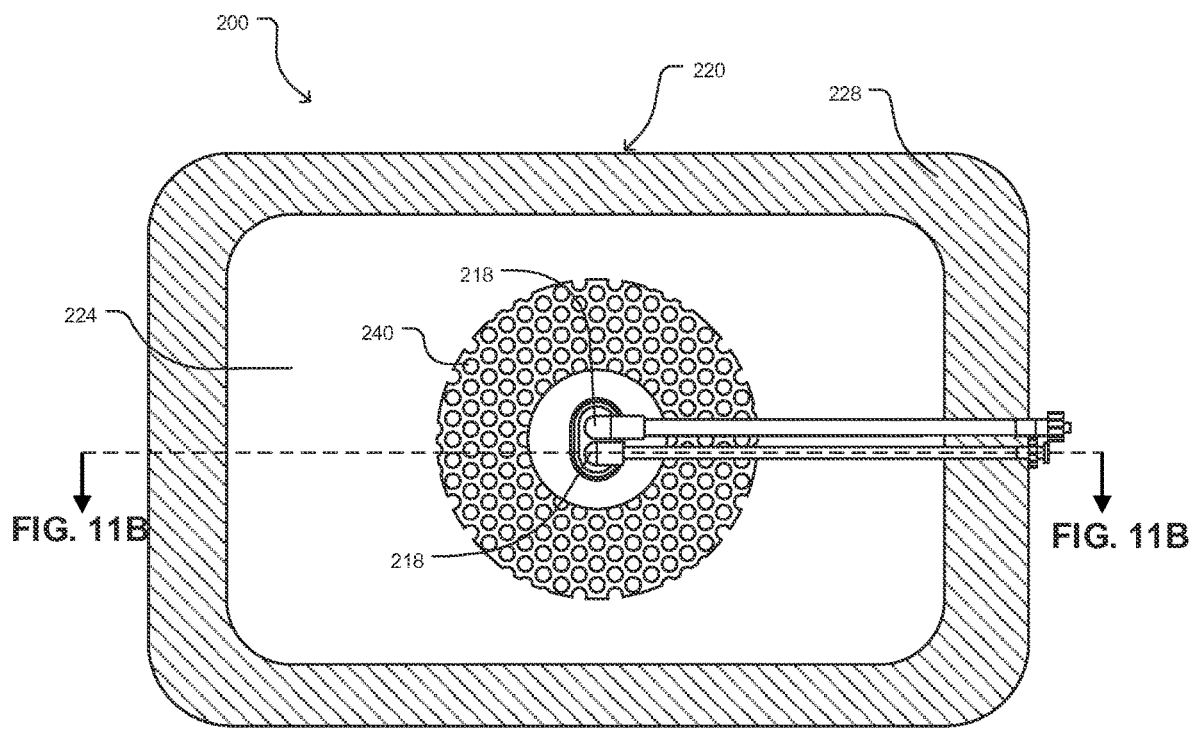
FIGS. 11A and 11B are top and cross-sectional views, respectively, of the system of FIG. 2.
Figure 11B:
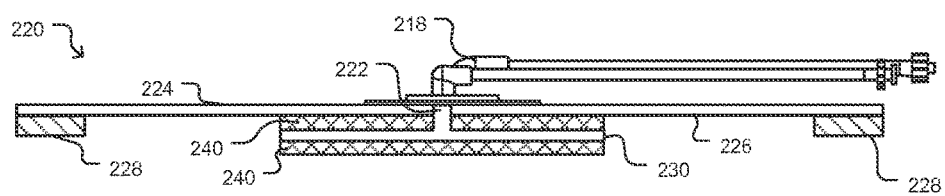

Referring to FIGS. 11A and 11B, the sealing layer 120 of the system 100 of FIG. 2 can be disposed above the netting layers 140 and the irrigation network 130 to create an air-tight seal over a wound (e.g., the wound 10 of FIG. 1). The sealing layer 120 includes two different adhesive materials: the gel adhesive 128 (e.g., an outer sealing layer) for sealing skin located proximate to the wound and the film barrier 124 (e.g., an inner sealing layer) that adheres to the wound and surrounding skin. The depicted film barrier generally makes up a central region of the sealing layer and includes two centrally located openings 122 to allow the manifolds 118 a fluid connection with the netting layers 140 and the irrigation assembly 130. The gel adhesive 128 can be disposed along the outer perimeter of one face of the film barrier 124.

Certain embodiments of the film barrier 124 may be composed of a transparent polymeric film, such as a polyurethane film (e.g., Tegaderm™), that covers the netting layers and the irrigation assembly within the wound. Some embodiments of the film barrier 124 are air and liquid impermeable for providing an air-tight or substantially air-tight seal to allow for negative pressure wound therapy. An air-tight seal can also help to control wound bleeding. Alternatively, in some embodiments, at least a portion of the system 100 (e.g., the film barrier 124) can be air-permeable, i.e., breathable, to allow air to pass through to a select area of the wound or surrounding skin. The film barrier 124 can be used to seal the dressing such that a practitioner can visually monitor the superficial surface of the wound after the dressing has been applied and without disrupting the placement of the dressing. In some embodiments, a wound-facing surface 126 (e.g., a first surface) of the film barrier 124 includes a low adherency adhesive that allows the sealing layer 120 to adhere to the skin once the film barrier 124 comes into contact with the skin, while still allowing for removal or re-positioning of the sealing layer 120 with low force detachment from the skin. In other embodiments, the wound-facing surface 126 does not include an adhesive.

In certain implementations, the film barrier 124 may be composed of an elastic material that allows the film barrier 124 to stretch. An elastic film barrier 124 can have improved sealing integrity as surrounding skin stretches and underlying muscles contract or relax with movements, subjecting shear and tensile stresses on the film barrier.

Still referring to FIGS. 11A and 11B, the gel adhesive 128 (i.e., outer sealing layer) can be an adhesive material applied along the outer periphery of the film barrier 124 to seal the sealing layer to a wound. The gel adhesive 128 may be disposed on the sealing layer 120 in various shapes and sizes. The gel adhesive 128 can be disposed on the sealing layer as a square, rectangular (e.g., a ribbon), or a circular shape. In some embodiments, the sealing layer includes a gel adhesive 128 that has a thickness and height ranging from about 1 mm to about 10 mm (e.g., from about 1 mm to about 2 mm, from about 2 mm to about 3 mm, from about 3 mm to about 4 mm, from about 4 mm to about 5 mm, from about 5 mm to about 6 mm, from about 6 mm to about 7 mm, from about 7 mm to about 8 mm, from about 8 mm to about 9 mm, from about 9 mm to about 10 mm). Certain embodiments of the gel adhesive 128 have a greater thickness (e.g., about 10 mm or greater than 10 mm) to increase the adherence of the sealing layer 120 to or around the wound. A thicker gel may, in some cases, prevent leaks for tissue surfaces associated with ridges, crevasses, rapid hair growth. In some embodiments, the thicker gel may also prevent leakage through apertures created by staples that may pierce through the sealing layer by sealing around the staples.

In some embodiments, the gel adhesive 128 has higher adherence to tissue than the adhesive surface of the film barrier. Certain embodiments of the gel adhesive 128 provide a stronger bond than the film barrier 124 since the gel adhesive may be adhered to uninjured skin near the wound. A stronger peripheral seal can reduce the need for using a stronger adhesive on the film barrier 124, which comes in contact with damaged, more sensitive tissue. In some embodiments, the gel adhesive 128 can be applied directly to a patient's skin at locations proximate to the wound and can be easily re-positioned, as desired. In some embodiments, the gel adhesive 128 can be composed of a hydrogel or a hydrocolloid, such as petrolatum. A hydrogel dressing or hydrocolloid dressing (e.g., Comfeel Plus Ulcer® manufactured by Coloplast, 'Duoderm®, Granuflex®, Ultec®, and Tegaderm Hydrocolloid® manufactured by 3M) can include various opaque dressing for wounds. In some cases, a hydrogel or hydrocolloid dressing can be biodegradeable, non-breathable, and/or adhere to the skin such that no separate taping is needed. The active surface of the dressing may be coated with a cross-linked adhesive mass containing a dispersion of gelatin, pectin and carboxy-methylcellulose together with other polymers and adhesives that form a flexible wafer. When in contact with wound exudate, the polysaccharides and other polymers of the dressing can absorb water and swell, forming a gel which is held within the structure of the adhesive matrix. The moist conditions produced under the dressing are intended to promote fibrinolysis, angiogenesis and wound healing, without causing softening and breaking down of tissue. The gel which is formed as a result of the absorption of wound exudate is not mobile and free running but held within the structure of the adhesive matrix. In various implementations, hydrocolloid dressings can be waterproof for allowing normal washing and bathing.

Figure 17A:
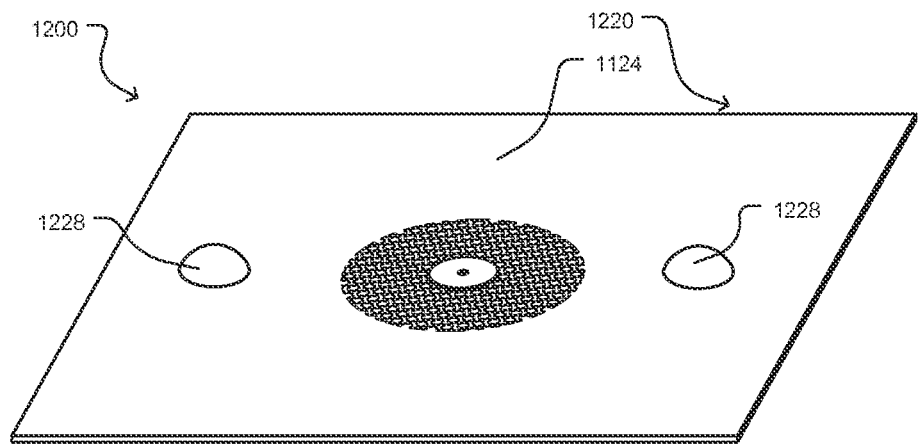
FIGS. 17A-17C show an example of a multilayered dressing system that includes adhesive weld spots for facilitating proper placing of the system.
Figure 17B:
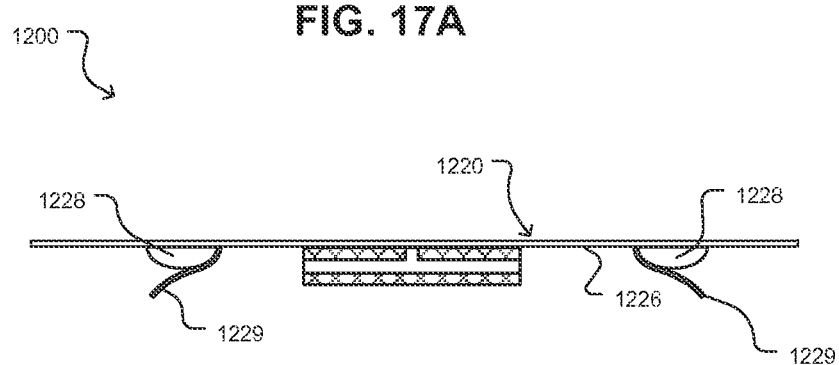
Figure 17C:
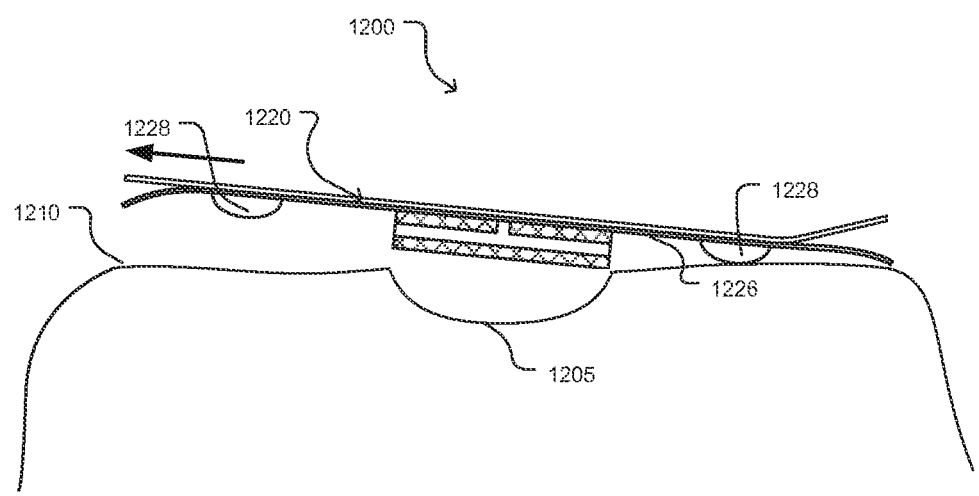

In certain implementations, the gel adhesive 128 can be located, for example, as a ribbon of sealant, along the outer perimeter of the film barrier 124. In other implementations, the gel adhesive 128 can be applied more centrally on the wound-facing surface of the film barrier, for example, adjacent to the dressing portions of the system. In some embodiments, the sealing layer can include multiple ribbons of the gel adhesive 128 along the wound-facing surface of the film barrier. Other gel adhesive 128 patterns can be used, such as gel spots (as best shown in FIGS. 17A-17C) or curvilinear patterns along at least portions of the wound-facing surface.

In a wound dressing application, peripheral skin areas near a wound may be subject to various preparations prior to applying the system to the wound. Skin preparation can include shaving the edges of the wound to allow for an airtight seal when the sealing layers of the system is applied.

In certain implementations, a surface modifier may be used with the system to improve its seal or prevent loss of its seal caused by stresses caused by a patient's movements, hair, dead tissue, and/or sweat accumulation. In some embodiments, a portion of the sealing layer (e.g., the film barrier 124 or gel adhesive 128) includes surface modifiers described herein. In some embodiments, before applying the system, a practitioner may optionally apply a surface modifier to the wound or surrounding skin. Surface modifiers include, but are not limited to, an adhesion promoter, a depilatory agent to prevent or reduce the likelihood of hair growth, an antiperspirant, or an exfoliator on undamaged skin having an intact epidermis that surrounds the wound. The surface modifiers can come in the form of a cream, lotion, paste, ointment, emulsion, gel, foam, or a liquid that may be applied by topical application such as spraying, painting, by injection, and/or by oral consumption using tablets or capsules. In some embodiments, the surface modifier may be impregnated within the sealing layer adhesive, e.g., the gel adhesive 128, to provide a sustained release of the surface modifier for a desired duration.

In some embodiments, the surface modifier can include a liquid medical adhesive, such as Mastisol® or Benzoin, to enhance and maintain a seal of the system to the surrounding skin.

In some embodiments, the surface modifier can include a depilatory agent to slow or prevent hair regrowth on the sealed skin, in particular, skin on facial or scalp areas. Antiperspirants can be also applied, in certain embodiments, to reduce the likelihood of or prevent sweating. In some embodiments, exemplary antiperspirants can include a topical application composed of aluminum chloride, such as Drysol, Xerac, and Bromi-lotion. In other embodiments, antiperspirants can be provided in the form medications such as Botox, to prevent sweating. Botox and other muscle contraction inhibitors in suitable amounts may be applied to the wound or surrounding tissues to prevent or reduce the likelihood of muscle contraction for reducing wound contracture, which causes wound widening.

Figure 12A:
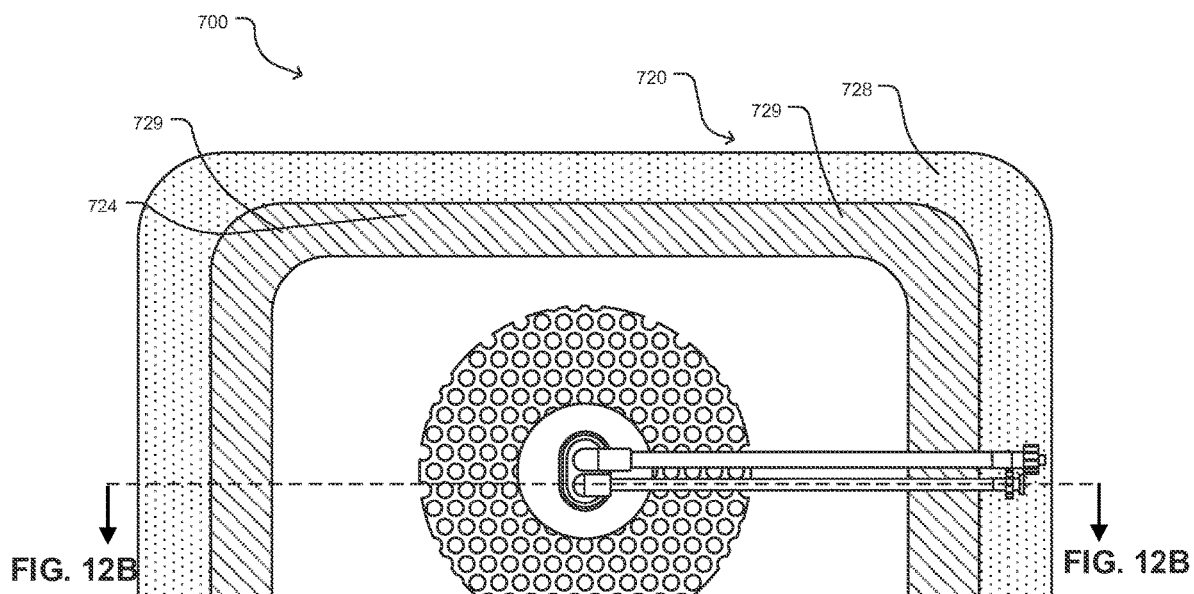
FIGS. 12A and 12B are top and cross-sectional views, respectively, of a second example of a multilayered dressing system.
Figure 12B:
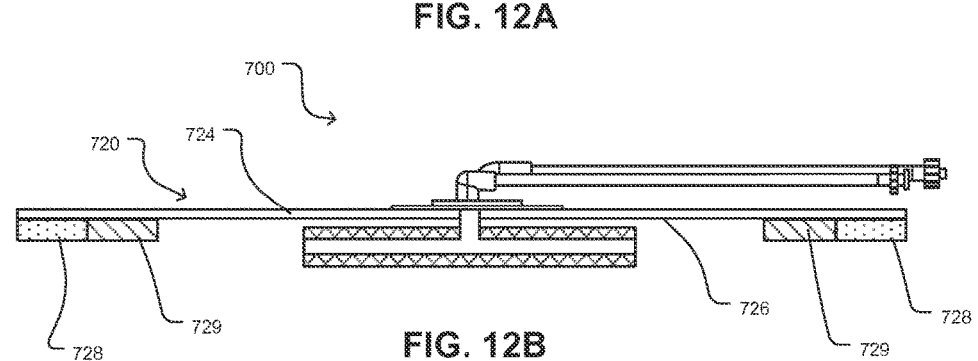

Referring to FIGS. 12A and 12B, another example of a system 700 includes a sealing layer 720 that includes a film barrier 724 (e.g., a first sealing layer) and two gel adhesives 728, 729 (e.g., a second sealing layer). The sealing layer 720 is similar to the sealing layer 120 shown in FIGS. 11A & 11B, with the exception of an additional gel adhesive 729. In some embodiments, the sealing layer 720 of the system 700 can include a first gel adhesive 728 and a second gel adhesive 729. The first gel adhesive 728 and the second gel adhesive 729 can be composed of the same or different gel adhesive materials described herein. For example, in some embodiments, the first gel adhesive 728 can be composed of a hydrogel and the second gel adhesive 729 can be composed of a hydrocolloid having a higher adherence to tissue when compared to an adhesive surface of the film barrier 747, but lower adherence to tissue when compared to the adherence of the hydrogel.

Referring to FIGS. 13 and 14, some examples of a system 800, 900 include sealing layers 820, 920 that have a film barrier 824, 924 and multiple applications of one or more gel adhesives 828, 928, 929. The sealing layers 820, 920 of FIGS. 13 and 14 are similar to the sealing layer shown in FIGS. 11A & 11B, with the exception of the gel adhesives 828, 928, 929.

Referring in particular to FIG. 13, the sealing layer 820 can include multiple applications of the gel adhesive 828 on the wound-facing surface 826 of the film barrier 824 such that each application of the gel adhesive 828 is spaced apart from one another. For example, the depicted sealing layer 820 of the system 800 includes three applications of the gel adhesive, each being spaced apart by a gap. Each gap allows space for expansion of the gel adhesive during use when the gel is compressed against a patient's skin and expands outwardly. Accordingly, the gap between the seals allows for expansion, as desired, in addition to increasing overall seal strength of the system to the patient's skin.

Referring to FIG. 14, some embodiments of the sealing layer 920 may include multiple gel adhesive applications 928, 929, for example, two, three, four, five or more than five different inner seals. Some sealing layers 920 include multiple inner seals having different seal materials, for example, the sealing layer of FIG. 14 includes five different gel applications 928, 929 composed of two different materials disposed in an alternating pattern. In some cases, a gel adhesive can be spaced apart from each other by a gap filled with a non-adhesive material, such as an antibiotic agent. For example, the depicted sealing layer can include three gel adhesives 928 and non-adhesive materials 929 disposed between the gel adhesives 929. FIG. 14 provides one example of gel adhesive configuration, but various other gel configurations may be contemplated by one skilled in the art.

Figure 15A:
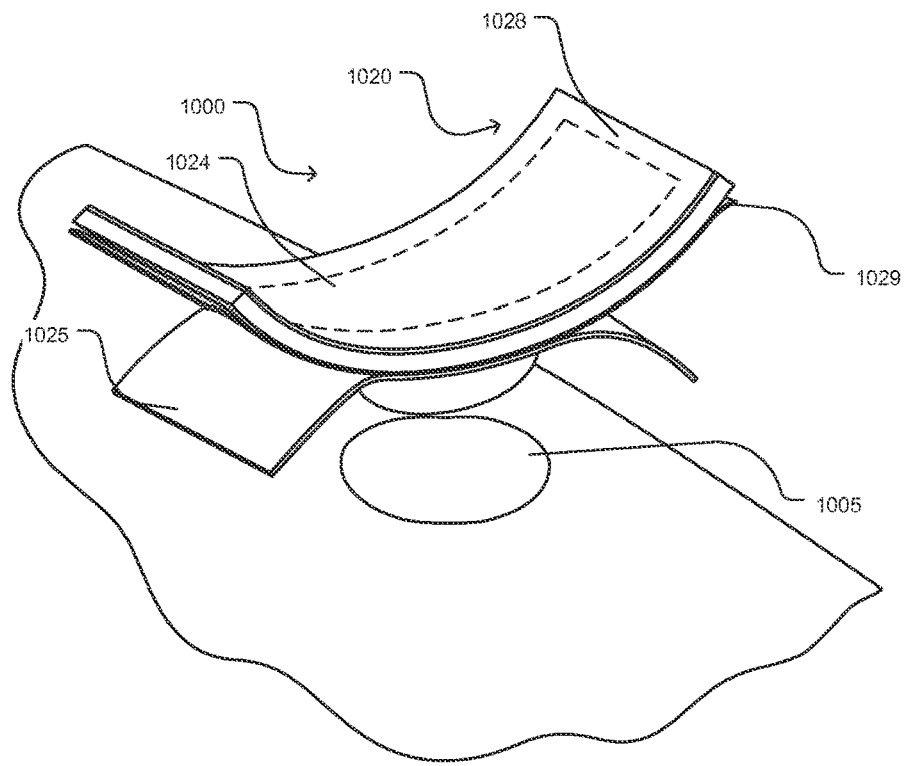
FIGS. 15A-15C are perspective and cross-sectional views of a multilayered dressing system as the system is being applied to a wound.
Figure 15B:
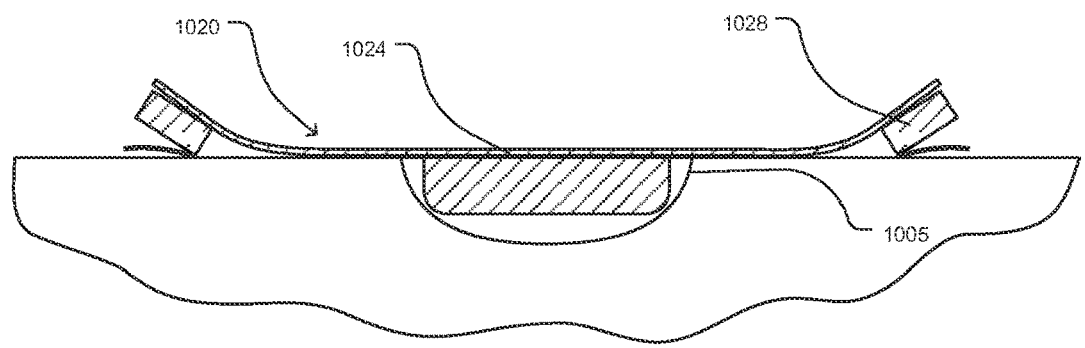
Figure 15C:
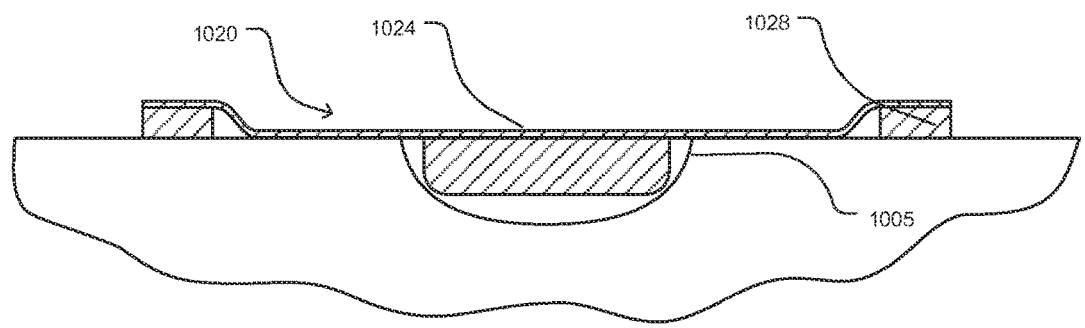

FIGS. 15A-15C show a generalized illustration of a system 1000 as it is being applied to a wound 1005. As shown in FIG. 15A, the system 1000 can include a sealing layer 1020 with multiple types of adhesives: a film barrier 1024 and a gel adhesive 1028. The film barrier 1024 can include a first backing 1025 to protect an adhesive surface on the wound-facing surface 1026 of the film barrier 1024 during shipping and handling prior to an application. In some embodiments, the adhesive surface of the film barrier 1024 is located at or near a central region of the sealing layer 1020 for adhering the system to the wound 1005. Certain embodiments of the system include the gel adhesive 1028 along the peripheral rim of the wound-facing surface 1026 of the film barrier 1024. The gel adhesive 1028 can include a second backing to protect a gel-like adhesive during shipping and handling prior to the application. During a medical procedure, the system 1000 may be placed onto a wound by first removing the first backing 1025 of the film barrier 1024, as shown in FIG. 15A, to expose the adhesive surface (e.g., the wound-facing surface 1026). The first backing 1025 exposes a wound-facing adhesive surface of the film barrier 1024. The adhesive surface of the film barrier 1024 can optionally include a pressure adhesive. Once the film barrier 1024 is placed onto the wound area, as shown in FIG. 15B, the second backing 1029 from the gel adhesive 1028 may be removed. As shown in FIG. 15C, the exposed gel adhesive 1028 can be placed into contact with the skin to hold the system 1000 in place while the wound heals.

Figure 16A:
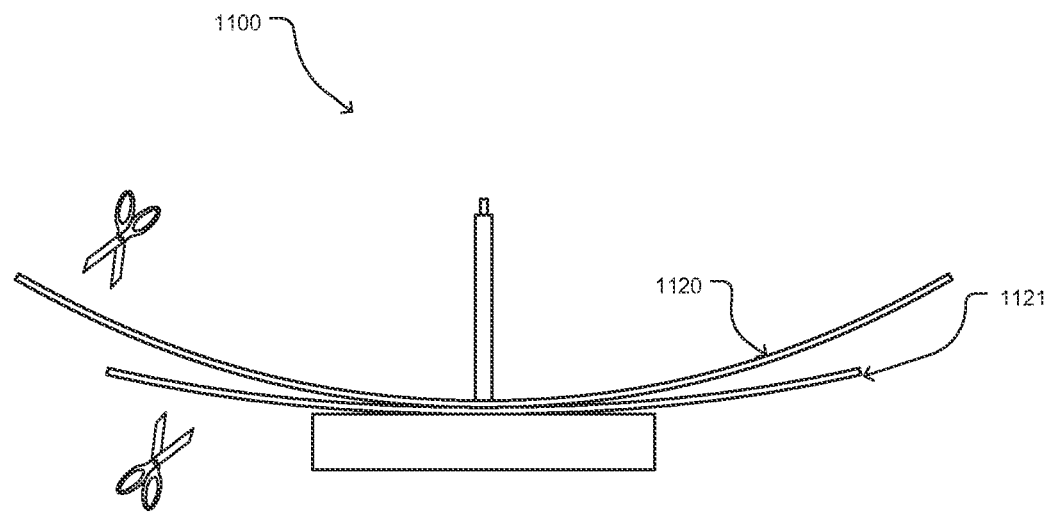
FIGS. 16A-16C show an example of a multilayered dressing system that can be tailor cut to a smaller size.
Figure 16B:
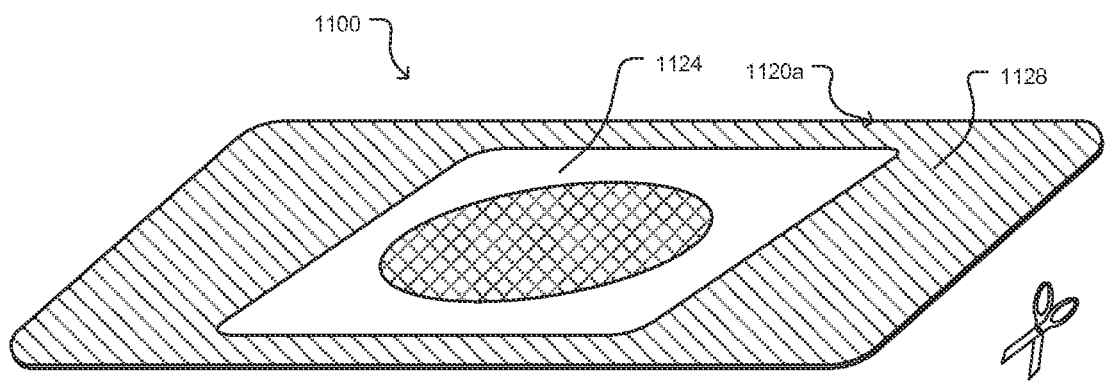
Figure 16C:
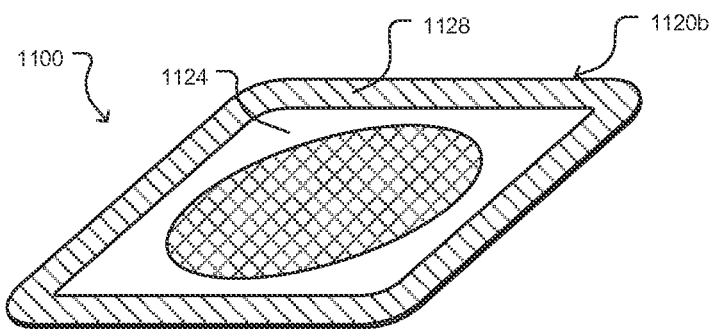

FIGS. 16A-16C show an example system 1100 having multiple sealing layers 1120, 1121 that can be tailor cut to smaller sizes. For example, some embodiments of a system (e.g., system 1100) can include scalable sealing layers (e.g., an outer sealing layer 1120 and an inner sealing layer 1121) having an original size and shape that can be cut into a smaller customized shape and size during an application. For example, as shown in FIGS. 16B and 16C, a larger, rectangular-shaped sealing layer 1120a can be cut into a smaller, square-shaped sealing layer 1120b when customizing the sealing layer 1120 to a patient's wound. In some embodiments, the outer sealing layer 1120 includes a gel adhesive 1128 on a portion or an entire wound-facing surface. In some embodiments, the second sealing layer 1121 includes a film barrier 1124 with an optional low adherency adhesive on a portion or an entire wound-facing surface.

FIGS. 17A-17C show an example of a system 1200 that includes gel spots 1228 disposed on a wound-facing surface 1226 of a sealing layer 1220 for securing the system 1200 over a wound 1205 during an application. The depicted sealing layer 1220 has two gel spots 1228 for releasably attaching the sealing layer 1220 to skin 1210 at a location proximate to the wound. The gel spots 1228 are positioned along the skin-facing surface 1226 of the sealing layer 1220 to facilitate placement of the system 1200 during an application procedure. Each gel spot 1228 can include a separate peelable backing 1229 to protect the gel spot 1228 during shipping and handling before use. During application of the system 1200, the backing 1229 may be removed from one gel spot 1228 such that a practitioner can adhere the gel spot 1228 to the patient's skin 1210. Once the one gel spot 1228 has been adhered, the practitioner can then manipulate the system 1200 such that the netting layers and the irrigation assembly are positioned within the wound 1205 and the remaining portion of sealing layer 1220 is positioned on the skin 1210 to create a tight seal over the wound 1205 before adhering the second gel spot 1228 to the skin 1210. In some embodiments, the system 1200 can include a sealing layer 1220 with one or more than two gel spots 1228, for example, three, four, five, ten, or more than ten gel spots. The shape of the gel spot 1228 can be circular, square, rectangular, triangular or polygonal.

A number of embodiments of the invention have been described. Nevertheless, it will be understood that various modifications may be made without departing from the scope of the invention. Accordingly, other embodiments are within the scope of the following claims.

What is claimed is:

1. A multilayered dressing system for negative pressure wound therapy, comprising:
    a hub including a manifold configured for connection with an inflow line that provides a first fluid pathway to an irrigation fluid source and an outflow line that provides a second fluid pathway to a vacuum source;
    a vacuum interface chamber defining a lumen in fluid communication with the first fluid pathway, the vacuum interface chamber comprising a series of risers that provide structural support and define intermediate fluid pathways between the second fluid pathway and a plurality of pores facing radially outward from a side of the vacuum interface chamber;
    a sealing layer positioned between the hub and the vacuum interface chamber, the sealing layer comprising a film having a first surface and a second surface, the first surface being coupled to the hub, the second surface comprising a gel adhesive disposed at one or more peripheral locations on the film;
    a perforated layer coupled to the second surface of the film of the sealing layer, the perforated layer defining a plurality of pores for fluid flow toward the vacuum interface chamber; and
    an irrigation network coupled to the perforated layer, the irrigation network including a plurality of tubes in fluid communication with the first fluid pathway via the lumen of the vacuum interface chamber, each tube defining a lumen extending from the lumen of the vacuum interface chamber to a radially outer edge of the perforated layer.

2. The system of claim 1, wherein the film of the sealing layer is a transparent plastic film comprising a polyurethane and wherein the film includes a clear adhesive on a wound-facing surface of the film.

3. The system of claim 1, wherein the gel adhesive of the sealing layer is located along the outer perimeter of the second surface of the film.

4. The system of claim 1, wherein the gel adhesive comprises a hydrogel or a hydrocolloid.

5. The system of claim 1, wherein the perforated layer is composed of silicone.

6. The system of claim 1, wherein the perforated layer includes pores each having a diameter of about 0.5 millimeters (mm) to about 2 mm.

7. The system of claim 6, wherein the gel adhesive is adapted to releasably bond the system along the one or more peripheral locations of the film to skin located around a wound.

8. The system of claim 1, wherein the sealing layer, the perforated layer and the irrigation network couple together as a single, composite unit such that no assembly is required during use.

9. The system of claim 1, wherein the irrigation network includes a body portion and eight outwardly radiating tubes extending from the body portion.

10. The system of claim 1, wherein the irrigation network includes two, three, four, five, six, seven, eight, nine, or ten tubes.

11. The system of claim 1, wherein the irrigation network is composed of a polyurethane.

12. The system of claim 1, wherein each tube of the irrigation network comprises two sealed edges that extend outwardly away from the lumen.

13. The system of claim 12, wherein the sealed edges of each tube of the irrigation network provide an attachment area for directly connecting the irrigation network to at least another portion of the system.

14. The system of claim 1, wherein the irrigation network includes an aperture for receiving an irrigant from the inflow line and the lumens of the plurality of tubes deliver the irrigant to the peripheral edges of a wound.

15. The system of claim 1, wherein at least one of the tubes include protrusions extending radially inward from an inner luminal wall of the lumen of the at least one tube of the plurality of tubes to provide flow path patency.

16. The system of claim 15, wherein the protrusions are located fully circumferentially along the inner walls of the lumen of the at least one tube of the plurality of tubes.

17. The system of claim 15, wherein the protrusions are located along a top portion or a bottom portion of the lumen of the at least one tube of the plurality of tubes.

18. The system of claim 15, wherein each protrusion is a short nub.

19. The system of claim 15, wherein each protrusion is an elongate finger-like extension.

20. The system of claim 1, wherein the plurality of pores are defined by a ventral floor of the vacuum interface chamber.

21. The system of claim 1, wherein the plurality of risers are configured to distribute a negative pressure from the outflow line.

22. A multilayered dressing assembly, comprising:
- a hub having a manifold configured for connection with an inflow line that provides a first fluid pathway to an irrigation fluid source and an outflow line that provides a second fluid pathway to a vacuum source;
- a vacuum interface chamber defining a lumen in fluid communication with the first fluid pathway, the vacuum interface chamber comprising a series of risers that provide structural support and define intermediate fluid pathways between the second fluid pathway and a plurality of pores facing radially outward from a side of the vacuum interface chamber;
- a sealing layer positioned between the hub and the vacuum interface chamber, the sealing layer having a first surface and a second surface, the first surface being coupled to the hub, the second surface comprising a gel adhesive for adhering the assembly to skin located proximate a wound;
- a netting layer coupled to the second surface of the sealing layer; and
- an irrigation network coupled to the netting layer.

23. The system of claim 22, wherein the gel adhesive is a hydrogel or a hydrocolloid.

24. The system of claim 23, wherein the gel adhesive comprises a surface modifier.

25. The system of claim 24, wherein the surface modifier is an adhesion promoter, a depilatory agent, an antiperspirant, or an exfoliator.

* * * * *